(12) United States Patent
Sun et al.

(10) Patent No.: US 7,301,335 B2
(45) Date of Patent: Nov. 27, 2007

(54) APPARATUS AND METHOD FOR EDDY-CURRENT MAGNETIC SCANNING A SURFACE TO DETECT SUB-SURFACE CRACKS AROUND A BOUNDARY

(75) Inventors: Yushi Sun, Superior, CO (US); Tianhe Ouyang, Superior, CO (US)

(73) Assignee: Innovative Materials Testing Technologies, Inc., Superior, CO (US)

( * ) Notice: Subject to any disclaimer, the term of this patent is extended or adjusted under 35 U.S.C. 154(b) by 153 days.

(21) Appl. No.: 11/114,507

(22) Filed: Apr. 25, 2005

(65) Prior Publication Data

US 2005/0237055 A1    Oct. 27, 2005

Related U.S. Application Data

(60) Provisional application No. 60/564,906, filed on Apr. 23, 2004.

(51) Int. Cl.
*G01N 27/82* (2006.01)

(52) U.S. Cl. .................. 324/240; 324/242; 324/232; 324/235

(58) Field of Classification Search ......... 324/217–243
See application file for complete search history.

(56) References Cited

U.S. PATENT DOCUMENTS

| | | | |
|---|---|---|---|
| 2,573,799 A | | 11/1951 | MacClean |
| 2,610,230 A | * | 9/1952 | Wiegand ................ 324/222 |
| 3,249,778 A | * | 5/1966 | McDougal ............... 310/105 |
| 3,996,510 A | | 12/1976 | Guichard |
| 4,271,393 A | * | 6/1981 | Hansen et al. ........... 324/240 |
| 4,495,466 A | * | 1/1985 | Lakin ...................... 324/242 |
| 4,496,904 A | * | 1/1985 | Harrison ................. 324/227 |

(Continued)

FOREIGN PATENT DOCUMENTS

CA    1208291    7/1986

(Continued)

OTHER PUBLICATIONS

Atherton, D A., et al., "Finite-Element Calculation for Shields in Remote-Field Eddy Current Tools", *Materials Evaluation*, 47 (Sep. 1989), 1084-1088.

(Continued)

*Primary Examiner*—Jay M Patidar
(74) *Attorney, Agent, or Firm*—Charles A. Lemaire; Lemaire Patent Law Firm, P.L.L.C.

(57) ABSTRACT

An RFEC excitation unit and sensor apparatus and method that facilitate detection of cracks or other anomalies within or under a surface and immediately next to an expected structure (such as a rivet) that would otherwise cause a signal change preventing detection of the cracks. In some embodiments, the apparatus includes actuators and control that move the apparatus and analyze sensed RFEC signals to determine the location of the rivet, and then to rotate (mechanically or electronically) the sensed signal and/or excitation signal to maintain a constant relationship to the edge of the rivet in order that signals from the rivet edge are suppressed and signals from the cracks are detected. In some embodiments, the excitation unit is maintained at the center of the rivet surface, and the sensor is moved around the rivet in a circle centered on the rivet.

29 Claims, 17 Drawing Sheets

U.S. PATENT DOCUMENTS

| | | | |
|---|---|---|---|
| 4,797,614 A | | 1/1989 | Nelson |
| 4,855,677 A | * | 8/1989 | Clark et al. ............... 324/238 |
| 5,264,733 A | | 11/1993 | Tigges |
| 5,399,968 A | * | 3/1995 | Sheppard et al. ........... 324/242 |
| 5,414,356 A | | 5/1995 | Yoshimura et al. |
| 5,554,933 A | * | 9/1996 | Logue ....................... 324/233 |
| 5,572,120 A | | 11/1996 | Takaishi et al. |
| 5,648,721 A | | 7/1997 | Wincheski et al. |
| 5,955,954 A | | 9/1999 | Keller |
| 6,002,251 A | | 12/1999 | Sun |
| 6,636,037 B1 | * | 10/2003 | Ou-Yang ................... 324/240 |

FOREIGN PATENT DOCUMENTS

| | | | |
|---|---|---|---|
| CN | ZL 90105697 | | 9/1993 |
| JP | 59-162448 | * | 9/1984 |

OTHER PUBLICATIONS

Lin, H Y., et al., "Application of "Zoom-in" Technique in 3D Remote Field Eddy Current Effect Calculation", *IEEE Trans. on Magnetics*, vol. 26, No. 2, (Mar. 1990),881-884.

Lord, W , et al., "A Finite Element Study of the Remote Field Eddy Current Phenomenon", *IEEE Transaction on Magnetics*, vol. 24, (Jan. 1988),435-438.

Lord, W , et al., "Physics of Remote Field Eddy Current Effect", *Review of Progress in Quantitative Nondestructive Evaluation*, vol. 7A, (1988),165-172.

Schmidt, T R., "The Remote Field Eddy Current Technique", *Materials Evaluation*, vol. 42, (Feb. 1984),225-230.

Sun, Y S., "Finite Element Study of Diffusion Energy Flow in Low-Frequency Eddy Current Fields", *Materials Evaluation*, vol. 47, (1989),87-92.

Von Rosen, E , et al., "Effect of Shielding and Exciter Coli Tilt on the Remote-Field Effect", *Materials Evaluation*, vol. 51, (Jan. 1993),66-71.

Chen, M J., et al., "A Finite Element Prediction of Possible Application of Pulse Excitation in Remote Field Eddy Current Nondestructive Inspection Devices", *International Journal of Applied Electromagnetics in Materials*, vol. 2, (1991),217-220.

Chen, M , et al.,"Pulsed RFEC Response", *IEEE Transaction on Magnetics*, vol. 28, No. 2, (Mar. 1992), 1430-1433.

Sun, Y , et al., "3-D Finite Element Modeling of the Remote Field Eddy current Effect", *Review of Progress in QNDE*, vol. 9A, (1990),319-326.

Sun, Y , et al., "A Remote Field Eddy Current NDT Probe for the Inspection of Metallic Plates", *Topical Conference Paper Summaries Book—ASNT's International Chemical and Petroleum Industry Inspection Technolgoy (JCPIIT) IV Topical Conference, 1995 and Materials Evaluation*, vol. 54/No. 4, (Apr. 1996),Appendix—09.

Sun, Y S., et al., "Computer Animated Presentation Visualizing The Phenomena in Remote Field Eddy Current Nondestructive Test Technique", *Electromagentic Forces and Applications*, (1992),203-206.

Sun, Y S., et al., "Crack Modeling Problem in Eddy Current Nondestructive Testing", *Electromagnetic Phenomena and Computation Techniques*, 173-182, (1992).

Sun, Y S., et al., "Efforts Towards Gaining a Better Understanding of The Remote Field Eddy Current Phenomenon and Expanding its Applications", *IEEE Transaction on Magnetics*, vol. 32, (1996),1589-1592.

Sun, Y S., et al., "Finite Element Modeling and Physics of Remote Field Eddy Current Responses for Axially Aligned Cracks", *IEEE Transaction of Magnetics*, vol. 28, (Jul. 1992), 1941-1947.

Sun, Y S., et al., "Improvement in Remote-Field Eddy Current Probe Structure", *Materials Evaluation*, vol. 50, (May 1992),600-604.

Sun, Y S., et al., "Inspection of Metallic Plates Using A Novel Remote Field Eddy Current NDT Probe", *Review of Progress in QNDE*, vol. 15A, (1996), 1137-1144.

Sun, Y S., et al., "Motion Induced Remote Field Eddy Current Effect in a Magnetostatic Nondestructive Testing Tool", *IEEE Transaction on Magnetics*, vol. 30, (Sep. 1994),3304-3307.

Sun, Y S., et al., "Progress in Developing RFEC Probe for Tank Bottom Inspection", *presented on ASNT's 1996 Spring Conference ASNT, Norfolk, VA*, (Mar. 19-21, 1996).

* cited by examiner

APPARATUS AND METHOD FOR EDDY-CURRENT MAGNETIC SCANNING A SURFACE TO DETECT SUB-SURFACE CRACKS AROUND A BOUNDARY

REFERENCE TO RELATED APPLICATIONS

This application claims benefit of U.S. Provisional Patent Application Ser. No. 60/564,906, entitled "METHOD AND AUTO-CENTERING PROBE FOR ENHANCED DETECTION OF SUB-SURFACE CRACKS AROUND RIVETS OR THE LIKE" filed Apr. 23, 2004, which is incorporated herein by reference in its entirety.

FIELD OF THE INVENTION

The present invention relates to remote-field eddy-current non-destructive testing, and more particularly, to probes that reject circumferential eddy-current waves or noise around a rivet or the like in order to better detect radial defects, and particularly sub-surface defects that are radially situated to the rivet.

BACKGROUND OF THE INVENTION

Magnetic fields create eddy currents within certain types of materials in objects in their path. The eddy currents in turn affect the magnetic field as observed from outside the objects. Cracks, discontinuities, holes, and changes in the material content all affect the eddy current flow within an object and also affect the magnetic field external to the object. Accordingly, magnetic fields can be used to scan materials to determine if the materials contain inconsistencies and anomalies (such as cracks or corrosion) that affect the magnetic field.

Remote-field eddy-current techniques can be used to scan materials. Remote-field eddy-current techniques (RFEC) generally involve detecting magnetic-field changes caused by anomalies on a surface of, and/or hidden in, a structure due to the RFEC technology's double-wall-transmission feature, while near-field eddy-current techniques generally involve detecting magnetic-field changes caused by anomalies on surface and near-surface areas due to the direct coupling of excitation unit(s) and sensor unit(s). Generally, the drive-sensor separation for an RFEC probe is greater than that of a non-RFEC probe; however, geometrical separation of the two coils is not a defining characteristic that distinguishes a "remote field" from a "near field" probe. Changes to an observed RFEC signal can be caused by undesirable anomalies, such as cracks, voids, internal or surface corrosion, embedded foreign objects, alloy-composition changes, etc., as well as by expected inherent features of the object being examined, such as joints and fasteners.

Users desire probes and techniques that are fast, reliable, accurate, easy to operate, and inexpensive. There is a need to extend the RFEC technique, as well as other eddy-current techniques for better noise control and small-flaw detection for inspection of various objects with different geometries, for example, those with flat geometry, or with approximately flat geometry in at least a local area, as well as objects with other surface geometries. In particular, there is a need to improve and/or automate detection of undesirable anomalies that are near expected inherent features of an object.

SUMMARY OF THE INVENTION

In some embodiments, the invention provides an apparatus that includes a magnetically shielded excitation unit that generates an alternating excitation magnetic signal; and one or more magnetically shielded sensors that are positioned adjacent the excitation unit and that are configured to detect a remote-field eddy-current signal due to the excitation magnetic signal, wherein the apparatus is configured to scan a surface (e.g., of a metal plate) having a structure (e.g., a joint, or a fastener such as a rivet) in order to detect anomalous signal changes around the structure in a manner that reduces signal changes due to a boundary between the structure and the surface.

In some embodiments, the invention provides a method that includes forcing an alternating excitation magnetic field into a surface, detecting a remote-field eddy-current signal resulting from the alternating excitation magnetic field at each of a plurality of positions on the surface surrounding a structure on the surface in a manner that reduces signal changes due to a boundary between the structure and the surface; and analyzing the detected signal from the plurality of positions to determine whether the surface contains an anomaly next to the structure.

In some embodiments, the invention provides a method that includes providing an apparatus comprising an excitation unit and one or more sensors next to the excitation unit; shielding the excitation unit and the one or more sensors to minimize detection of signals other than remote-field eddy-current signals by the one or more sensors; and configuring the excitation unit and the one or more sensors to detect anomalous signal changes around a structure in a surface in a manner that reduces signal changes due to a boundary between the structure and the surface.

In some embodiments, the invention provides an apparatus that includes means for forcing an alternating excitation magnetic field into a surface; means for detecting a remote-field eddy-current signal resulting from the alternating excitation magnetic field at each of a plurality of positions on the surface surrounding a structure in the surface in a manner that reduces signal changes due to a boundary between the structure and the surface; and means for analyzing the detected signal from the plurality of positions to determine whether the surface contains an anomaly next to the structure.

DETAILED DESCRIPTION OF THE INVENTION

Figure 1A:
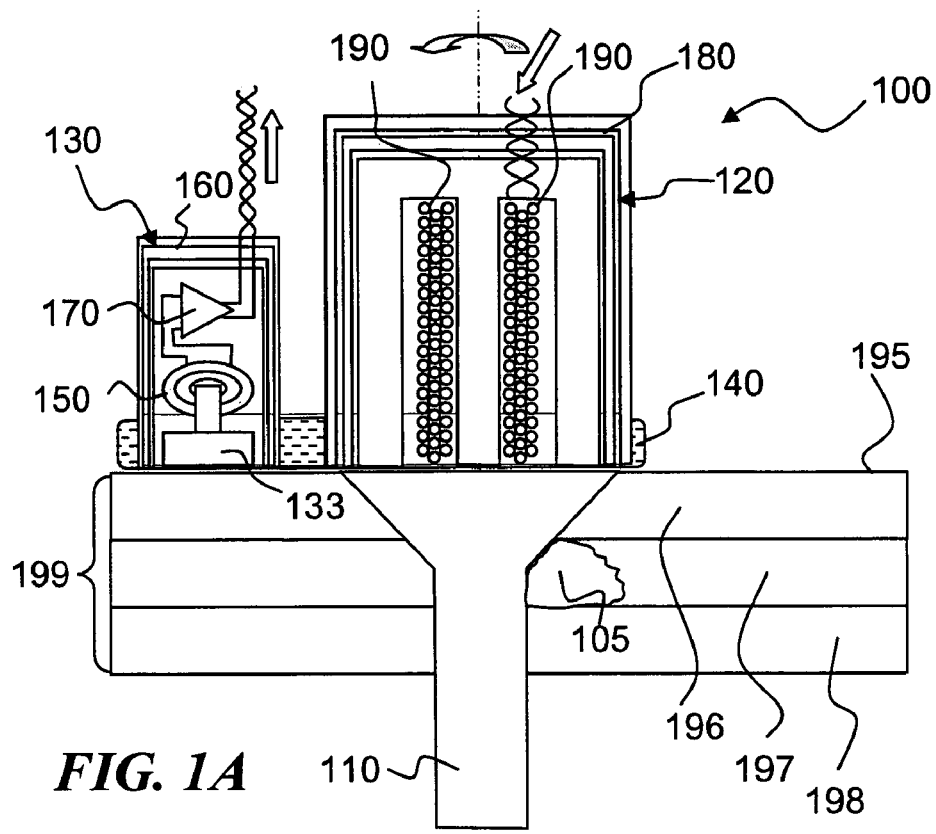
FIG. 1A is a side-view of an apparatus 100 having a sensor that is positioned to be rotated around an excitation unit that is positioned over a structure that penetrates a surface of an object.

The invention provides methods and apparatuses that can be used to scan an object for an anomaly. Generally, an apparatus of the invention is placed onto a surface of the object to be scanned so that an excitation unit that is a part of the apparatus is positioned to force an alternating excitation magnetic field into the object. The magnetic field produces near-field eddy currents that can be detected in close proximity to the excitation unit and remote-field eddy-currents that can be detected further away from the excitation unit relative to the near-field eddy-currents. A sensor that is part of the apparatus is positioned to detect the remote-field eddy-currents. Detection of the remote-field eddy-currents can be improved by shielding the sensor from the near-field eddy-currents.

The amplitude and intensity of the remote-field eddy-current will stay substantially constant at positions that are substantially radially equidistant from the excitation unit if the magnetic transmission characteristics of the material making up the object being scanned are substantially constant. However, anomalies in the material making up the object being scanned cause the magnetic transmission characteristics of the material being scanned to change at the point of the anomaly. Accordingly, anomalies can be detected by determining if the magnetic transmission characteristics of the material being scanned are consistent with the presence or absence of an anomaly.

Through use of the methods and apparatuses of the invention, anomalies that are exposed on a surface can be detected. Anomalies that are present below the surface of a layer of material making up the object being scanned can also be detected. For example, a sheet or plate of material, such as metal, can be scanned to determine if there are anomalies within the sheet of metal. Examples of such anomalies include differences in composition of the material being scanned that are caused by contaminants such as minerals, other metals, changes in the percentages of metals in an alloy, and the like. Anomalies can also be detected that are due to physical differences in the material being scanned such as cracks, bubbles, fissures, cavities, and the like.

In some embodiments, the methods and apparatuses of the invention can be used to scan a multilayered object. Accordingly, anomalies that are located on the surface of the object can be detected. Anomalies that are present below the surface of a layer of material making up the object being scanned can also be detected. Accordingly, the present invention provides methods and apparatuses that can be used to scan multilayered materials and laminates for anomalies.

The methods and apparatuses of the invention can be used to scan materials that are hidden or masked by a structure, such as a fastener, that is in contact with the material being scanned. For example, fasteners are often times used in the fabrication of objects that contact the surface of a layer of material that is used to construct an object. Examples of such fasteners include rivets, bolts, screws, and the like. The present methods and apparatuses can be used to scan material that is hidden below a fastener or next to the fastener. For example, through use of the invention, an aircraft wing can be scanned to determine if cracks or fissures have occurred within the wing at a position that is hidden beneath a rivet used to construct the wing. Such a use helps to insure the safety of aircraft for the transportation of passengers and cargo. In other examples, the invention can be used to scan a fuel tank to determine if the fuel tank has an unseen fracture that is hidden by rivets used to construct the tank that could cause the fuel tank to rupture and cause a deadly accident. In other examples, the invention can be used to scan a tank for fractures and other anomalies occurring in one or more layers of material used to construct a multilayered tank or vessel that could weaken the tank and cause it to leak or rupture. This ability of scan a tank for structural weakness is thought to be valuable in situations where the tanks are used to contain flammable or toxic materials. There are many other instances where the invention can be used to scan an object or material for an anomaly that would be recognized and appreciated by those of skill in the art.

Conventional techniques for scanning an object using RFEC or EC technologies present a problem when trying to detect anomalies next to or near expected inherent features of an object such as one or more metal sheets having a rivet that holds them together since, when moving a probe across the boundary between the top sheet and the rivet there is a relatively large signal change due to the probe crossing the rivet-sheet boundary. This boundary-caused signal change will mask any signal change that would be caused by an anomaly such as a small crack in an underlying sheet, if the crack is next to the rivet.

Some embodiments of the present invention enable detection of cracks and other anomalies next to or near expected inherent features by moving the magnetic sensor, the magnetic excitation unit, or both, along, parallel to, or at a constant distance from the boundary between the inherent features and the rest of the surface. For example, in some embodiments, the excitation unit can be kept substantially centered on a rivet head, while the magnetic sensor can be rotated around the rivet. If there are no anomalies, the sensed AC signal will be of substantially constant phase and amplitude. If, however, there is a crack or corrosion on one side, the sensed AC signal will vary in phase and/or amplitude as the sensor passes over the anomaly.

In the following detailed description of the preferred embodiments, reference is made to the accompanying drawings that form a part hereof, and in which are shown by way of illustration specific embodiments in which the invention may be practiced. It is to be understood that other embodiments may be utilized and structural changes may be made without departing from the scope of the present invention.

Excitation Units

In some embodiments, an apparatus includes one or more excitation units. In some embodiments, an excitation unit is an electromagnet coil device, such as a partially shielded electromagnet (e.g., substantially shielded on all sides of the excitation unit except a face that faces the object being examined) driven by an AC current of an appropriate frequency and magnitude, that can force an alternating magnetic field into an object. Various types of excitation units are known in the art and have been described in, for example, U.S. Pat. Nos. 6,636,037 and 6,002,251, both of which are incorporated by reference herein. Generally, an excitation unit includes an electronic excitation driver circuit that provides one or more phases of an A.C. electric excitation signal to drive one or more electro-magnet excitation coils in the excitation unit to generate an alternating magnetic excitation signal. In other embodiments, the excitation unit can include a permanent magnet that is physically rotated at an appropriate speed within shielding in order to obtain the alternating magnetic excitation field (rather than using an electromagnet driven by an AC electric signal).

In some embodiments, a magnetic excitation signal is in the form of an alternating magnetic field, which is used to scan an object by forcing the alternating magnetic field into the object to create eddy-currents and fields in the object. When the magnetic field and the eddy-currents and fields interact with an anomaly, such as a rivet or a crack or a thinning of a sheet of metal, the magnetic field at the surface above that anomaly is affected, in both phase and amplitude.

In some embodiments, the alternating magnetic field is an "absolute" alternating field, wherein a single-pole electromagnet is driven with a single-phase electrical signal. Over time, such a magnetic field travels radially outward, along and within a conducting object. For example, such fields propagate relative to a detector along the line between an excitation unit and the detector (i.e., radially outward). To detect anomalies, in some embodiments, such a probe is moved such that the excitation unit remains centered on a rivet, and the sensor unit is moved around the rivet along a line that is coincident with, or at a substantially constant distance from, the rivet-surface boundary. In other embodiments, such a probe is moved such that the sensor unit remains centered on a rivet, and the excitation unit is moved around the rivet along a line that is coincident with, or at a substantially constant distance from, the rivet-surface boundary, in order to move the excitation field around the rivet such that an anomaly will cause a change in the signal received by the sensor. In other embodiments, a rotating magnetic field (a magnetic field that has a phase change such that the point of constant phase moved around a closed path such as a circle) is provided by a stationary probe, wherein the excitation field is generated by a plurality of coils (arranged, for example, along a circle), each coil driven with a different phase of an excitation signal (i.e., the plurality of coils are driven by synchronized A.C. signals having a constant phase difference one to another), such that a phase front of the signal is moved along a line around the circumference of the face of an excitation coil unit ((e.g., in some embodiments, each excitation signal having a phase that is 60 degrees (for a six-phase excitation signal) or 120 degrees (for a three-phase excitation signal) offset from the phase of the adjacent signal)). In some embodiments, such fields propagate relative to a detector along, or at a tangent to, the line between the excitation unit and the detector. In yet other embodiments, a traveling magnetic field (a magnetic field that has a phase change such that the point of constant phase moved along a line, such as a straight line (however, the line need not be straight) is provided, wherein the field is generated by a plurality of coils that are each driven with a different phase of an excitation signal such that a phase front of the signal moves linearly along the face of the excitation coil unit (wherein each of three coils is driven by a phase that is 120 degrees offset from the last phase of the signal). Such fields propagate relative to each of one or more detectors linearly between the excitation unit and the respective detector.

In some embodiments, an excitation unit can generate a rotating excitation magnetic field (i.e., the field traveling or moving in a circumferential direction relative to the planar face, also called a planar rotating magnetic field). In these embodiments, an excitation unit can include an outer cup-shaped copper shield having, e.g., six pockets, each pocket containing a ferrite core with each ferrite core having a respective coil. In one embodiment, the copper shield includes six pockets that do not penetrate through the copper shield. Each pocket can contain its own ferrite core. In these embodiments, a three-phase or six-phase excitation signal is used. In some such embodiments (for example, a three-phase excitation circuit), a look-up table can contain digital values corresponding to successive points along a sine wave, and three digital-to-analog (D/A) converters are loaded with values from the table (e.g., the first D/A converter is fed values starting at 0 degrees, the second D/A converter is fed values starting at 120 degrees, and the third D/A converter is fed values starting at 240 degrees). For six-phase excitation, in some embodiments, three D/A converters are used, and the three signals are inverted to provide the other three phases (the inverted 0-degree signal provides the 180-degree phase, the inverted 240-degree signal provides the 60-degree phase, and the inverted 120-degree signal provides the 300-degree phase), for a total of six phases. In other embodiments, an off-the-shelf sine-and-cosine generator are used to provide 0 degree and 90 degree phases of the excitation signal, respectively, and the inverted versions of these signals provide the 180 and 270 degree phases respectively, for a total of four phases. This can provide a lower-cost signal source. In such embodiments, four, eight, twelve (or other multiple of four) ferrite cores are used, arranged in a circle. In some such embodiments, two or more sensors are arranged around the periphery of the excitation unit to allow sensing of the field to be scanned (moved) around the probe without moving the probe. In some embodiments, by not moving the probe, a cleaner (having less noise and variation) signal can be obtained than if the probe is moved during the measurement.

In some embodiments, an excitation unit includes a cup-shaped copper shield that includes a pocket. In some embodiments, the shield is a layered structure having one or more copper layers and one or more layers of a different metal such as aluminum or steel. The pocket can enclose a plurality of individual coils, the coils being on individual prongs or fingers of a ferromagnetic core having a shared or common back section In some embodiments, two or more linear excitation units are used in a parallel orientation on either side of one or more sensors which are located between the excitation units in order to obtain a more uniform traveling magnetic wave. In some embodiments, the plurality of core fingers and coils are aligned along a straight line to generate a straight linear traveling wave.

In other embodiments, the plurality of core fingers and coils are aligned along other open or closed shapes (and having either a planar face or a non-planar face) such as polygons or curves in a plane, or along a line that is not in a single plane, depending on the object to be measured.

In some embodiments, the ferrite core of the excitation unit uses an E-shaped ferromagnetic-core block having twelve coils, each of which is formed around its own respective prong of the multi-pronged E-shaped ferromagnetic core. In some embodiments of the excitation unit, the excitation signal driving the coils is a multi-phase sign wave signal such that the magnetic field generated by the excitation unit travels in a rotating fashion or a linear fashion. In some embodiments, a four-phase excitation signal is used; in other embodiments, a three-phase or six-phase or N-phase excitation signal is used. A single sine-value lookup table (e.g., read-only memory) can be used in some embodiments to load values into N D/A converters (or N/2 D/A converters each feeding an inverter to each provide two phases), in order to generate an arbitrary number of phases to drive a multi-phase excitation probe (either linear or rotating).

Magnetic Core for an Excitation Unit

In some embodiments, a single excitation coil is used in the excitation unit, and is driven by a single-phase AC electric signal. In other embodiments, two or more coils are used: a primary excitation coil is driven by one phase of an AC electric signal, and an auxiliary coil is driven by another phase of the AC electric signal and used to shape and direct the magnetic field into the object being inspected, as described in U.S. Pat. No. 6,002,251 by Yushi Sun, which is incorporated herein by reference. In some embodiments using RFEC probes, the excitation magnetic field is forced from the excitation unit, through the object being sensed, such that a portion of the field then passes back through the object at the sensor unit(s), thus providing the energy double transmission. As such a probe passes over portions of the object that provide a constant magnetic path between the excitation unit and the sensor unit, the phase and amplitude of the sensed signal remain constant. In other embodiments, the sensor is located in a position relative to the excitation unit such that the local eddy-current (EC) signal is sensed. If either such probe (RFEC or EC) moves across a boundary (such as a crack, or the joint between a rivet and the surrounding metal) or there is some other change in the magnetic path between the excitation unit and the sensor unit, the phase and amplitude of the sensed signal will change, and this signal change can be analyzed to obtain information about the internal structure of the object.

In some embodiments, the core is made of high permeability and low-conducting or nonconducting material(s). In some embodiments, the core is made of a single whole piece of a ferromagnetic material, e.g., ferrite.

In some embodiments, the core provides a substantially closed magnetic circuit. In some embodiments, the core and its magnetic circuit can be of any suitable shape having an opening which faces the air-gap (called the "sensing face") towards the object under inspection, and a highly conducting shield (made from, for example, aluminum and/or copper) which covers substantially all of the rest of the excitation core.

In one embodiment, the excitation unit is shielded. Shielding can be made from one or more layers of material such as aluminum, copper, steel, and/or other suitable magnetic and electrically shielding materials. Highly-conducting materials laminated with alternating layers of ferromagnetic materials are used to enhance the shielding effects in some embodiments.

Current in Excitation Coil

The frequency of the AC current applied to an excitation unit in order to generate a magnetic field can be varied in accordance with the material being scanned. For example, a low frequency, e.g., in the range of approximately 10 Hz-150 Hz can be used to scan carbon-steel plates, for example. In other embodiments, a frequency of up to approximately 4,000,000 Hz can be used for non-ferro-magnetic plates or sheets, such as aircraft aluminum alloys. In some embodiments, frequencies as low as about 10 hertz or lower are used in order to penetrate and inspect thicker plates. In other embodiments, frequencies of 4 MHz or higher are used for inspection of surfaces structures.

TABLE 1

TYPICAL FREQUENCY RANGES FOR SOME EMBODIMENTS

| Material | Thickness | Suggested frequency range |
|---|---|---|
| Al | Surface | 200 kHz-800 kHz |
| Al | <0.020" | 20 kHz or higher |
| Al | 0.060" | 1.0-8.0 kHz |
| Al | 0.120" | 0.4-2.0 kHz |
| Al | 0.200" | 0.2-0.8 kHz |
| Al | >0.300" | 0.1-0.4 kHz |
| Stainless Steel (SS) | Surface | 500 Hz-1 MHz |
| SS | Others | 5-10 times Al |
| Ti | Surface | 1 MHz-4 Mhz |
| Ti | Others | 10-30 times Al |
| Carbon Steel (CT) | <0.02" | 400 Hz-2 kHz |
| CT | 0.100" | 40 Hz-200 Hz |
| CT | >0.200" | <20 Hz |

In some embodiments, suitable frequencies are empirically determined, and may lie outside the ranges suggested in Table 1.

Sensors

Many types of sensors may be used in conjunction with the invention. For example, in some embodiments a magnetic sensor or sensors can include sensor coils that are mounted on a ferromagnetic core.

In some embodiments, a sensor includes one or more pickup coils that each has a magnetic core that is non-conducting or weakly conducting and a highly conducting shield that can be constructed from a material such as aluminum.

A sensor can include a wound-wire coil and a core which is used to shape or guide the field detected by the coil or coils. In another embodiment, in order to provide a more sensitive detector, a sensor can include a magneto-resistive (MR) sensor such as are known in the magnetic-sensing art (one example of such sensors are MR heads used in some hard-disk data drives), giant magneto-resistive elements, Hall elements, or other suitable magnetic sensors.

A sensor can be shielded. Shielding can be made from one or more layers of material such as aluminum, copper, steel, and/or other suitable magnetic and electrically shielding materials. Highly-conducting materials laminated with alternating layers of ferromagnetic materials are used to enhance the shielding effects in some embodiments.

A core used within a sensor can be of various shapes. For example a U-shaped core can be used for making an absolute sensor or a differential sensor, while an E-shaped core can be used for making differential sensors of various structures. An I-shaped core can also be used for making an absolutely sensor, however, it may have lower sensitivity than other sensors.

A sensor can be connected to an amplifier. Such an amplifier typically includes an operational amplifier and a gain-setting resistor. In one embodiment, an LT1167A low-noise operational amplifier (available from Linear Technologies, Inc.) is used that is wired to a printed circuit board with an appropriate gain-setting circuit (e.g., replacing the gain-setting resistor) to provide the desired amplification factor and stability. In some embodiments, a capacitor (e.g., 100 picoFarads) is wired across a coil to reduce high-frequency noise (i.e., this provides a low-pass filter function). In some embodiments, suitable offset-nulling circuitry is also used to reduce offset errors and drift. In some embodiments, the operational amplifier can be provided with plus and minus voltage ($V^+$ and $V^-$) power. In other embodiments, a sensor can include one or more giant magneto-resistive (GMR) sensors, magneto-resistive (MR) sensors, or Hall-element sensors along with suitable biasing circuitry. In some embodiments, connecting cables include grounded shields surrounding each separate signal conductor, for additional grounding and shielding.

Shielding

Shielding can be made from one or more layers of material such as aluminum, copper, steel, and/or other suitable magnetic and electrically shielding materials. Highly-conducting materials laminated with alternating layers of ferromagnetic materials are used to enhance the shielding effects in some embodiments.

In some embodiments, the invention provides pre-amplification to increase the sensitivity of detection where the preamplifier circuit optionally is not shielded. In some other embodiments, the invention provides shielded pre-amplification (e.g., preamplification in the sensor unit and within its shielding), in order to increase the sensitivity of detection. There is a need to detect very small signals that are associated with the eddy-current effects on the alternating magnetic field from excitation unit. In some embodiments, the received signal is on the order of a fraction of a microvolt to a few microvolts. In some embodiments, a signal-conditioning circuit provides an amplification of 1000 times. In other embodiments, signal-conditioning circuit provides an amplification of 100 times. In some embodiments, signal-conditioning circuit also provides a low-pass filter function, in order to remove high-frequency noise.

Display

Some embodiments include a display that shows graphical displays of phase and amplitude or the relative phases of the output and input signals, and/or other indications of the real and imaginary portions of a received signal, as compared to a phase reference for the excitation unit. These displayed signals can be used to detect anomalies in the object being scanned.

Some embodiments include a display that indicates the position of an excitation unit, a sensor, or both an excitation unit and a sensor relative to a position or structure on an object that is to be scanned. For example, a display can be prepared that will indicate if an excitation unit, a sensor, or both an excitation unit and a sensor are centered on a structure. In addition, a display can be prepared that will indicate the direction in which an apparatus of the invention should be moved to center the apparatus on a structure.

Calibration Method

In some embodiments, a simple probe and output unit (having simple graphical or audible output) is provided to an operator who practices with a test object having known cracks or thinning, and learns to recognize the indications of flaws. This provides the simplest instrument, but requires a trained operator. In other embodiments, an apparatus is calibrated by scanning a known control object or surface, and the indications of the received good signal are recorded. Then a similar object having possible flaws is scanned using the same or a similar pattern of scanning, and the resulting received signal is compared to the known good signal to detect differences indicative of flaws. In yet other embodiments, the signatures of certain flaws are recorded by an apparatus (e.g., within a memory forming part of the apparatus), and a pattern-recognition program is used to distinguish "good" signals (indicative of non-flawed parts) from "bad" signals (indicative of flaws), and an indication or the result is provided to the display.

Scanning Method

One aspect of the present invention provides a method of scanning an object for an anomaly. This method includes shielding an excitation coil on substantially all sides except an emission face, shielding a sensor on substantially all sides except a reception face to form a probe, and transmitting an alternating magnetic signal at a plurality of positions on the object from the shielded excitation coil such that the alternating magnetic signal is modified by the conducting object. The method also includes receiving the alternating magnetic signal as modified by the object into the shielded sensor, converting the received alternating magnetic signal into a first electrical signal within the shielded sensor, shielding a signal-conditioning circuit within the apparatus on substantially all sides, providing electrical power to the shielded signal-conditioning circuit within the apparatus, amplifying the first electrical signal with a signal-conditioning circuit to create a second electrical signal. In some embodiments, an Eddyscope processes and demodulates the second signal to obtain the final electric signal. Analyzing phase and amplitude components of the final electrical signal provides an indication of the flaw. For example, in some embodiments, the probe is moved in a raster-scan pattern across a surface of the object being scanned. In some embodiments, multiple scans are performed, each having the sensor at a different angle relative to the excitation unit. In some embodiments, a relatively course raster pattern (using, e.g., relatively large X spacings between each Y line scan of the object) is initially used to determine the general position and orientation of features such as rivets in an object, and then finer raster scans (using, e.g., relatively small X spacings between each relatively short Y line scan) are performed in the immediate vicinity of each feature located in the initial scan. In some embodiments, once the exact location and nature of each feature has been determined using this process, the probe is moved such that, for example, the excitation unit is moved to the center of the feature (such as a rivet, for example), and the sensor is moved along a closed (or, in some embodiments, an open-ended) path that follows along, or at a substantially constant distance from, the perimeter of the object.

One type of object that can be examined by some embodiments of the present invention is the outer metal skin of an aircraft (for example, the rotor blade of a helicopter). Such objects can include multiple layers of similar or dissimilar metals (such as aluminum, titanium, and steel). In some embodiments, a paint layer and/or applique layer extends across the area being scanned (i.e., such layers, in some embodiments, are between the apparatus and the surface of the object being scanned). An anomaly can still be detected whether or not such paint and/or applique layers are present. Cracks or layer thinning (for example due to metal fatigue or corrosion) can be detected because the phase and/or amplitude of the detected signal are changed due to such anomalies. In other embodiments, pattern recognition software can be used to analyze and augment the displayed signals to identify signals indicative of flaws. Further, both cracks in the surface metal of an object (e.g., crack) as well as cracks in underlying (hidden) sheets provide signatures that are different than signals of objects that do not have such flaws.

Some embodiments of the invention provides an apparatus that includes a magnetically shielded excitation unit that generates an alternating excitation magnetic signal, and one or more magnetically shielded sensors that are positioned adjacent the excitation unit and that are configured to detect a remote-field eddy-current signal due to the excitation magnetic signal, wherein the apparatus is configured to scan a surface having a structure in order to detect anomalous signal changes around the structure in a manner that reduces signal changes due to a boundary between the structure and the surface.

FIG. 1A is a schematic cross-sectional elevation side view (along section line 1A shown in FIG. 1B) that illustrates one embodiment of an apparatus or probe 100 of the invention Probe 100 is positioned on the surface 195 of an object 199 that contains an anomaly 105 (for example, a small crack in layer 195 next to fastener 110). The exemplary object 199 includes a fastener 110 (for example, a bolt or rivet) that penetrates and fastens multiple adjacent layers 196, 197 and 198 of the object 199. In some embodiments, fastener 110 is mushroomed at its bottom end, such as shown for rivet 710 of FIG. 7A. The apparatus 100 includes at least an excitation unit 120 and a sensor 130. The excitation unit 120 illustrated in FIG. 1A includes a cylindrical excitation coil 190 (shown in cross section in FIG. 1A) and excitation-unit shielding 180. The sensor 130 illustrated in FIG. 1A includes an amplifier 170, a coil 150 and sensor shielding 160. In some embodiments, a base 140 made of dielectric material and/or magnetic shielding is used to mount and/or hold excitation unit 120 and sensor 130 in a fixed relationship to one another, and in use, is positioned on the surface 195 of the object 199, as shown in FIG. 1A, so it can be rotated around fastener 110. In some embodiments, base 140 is configured (e.g., by including an indentation or protruding point that can fit or be kept centered on the fastener head) to facilitate moving sensor 130 around a perimeter of fastener 110 while keeping excitation unit 120 centered on fastener 110. The excitation unit 120 is maintained substantially centered over the fastener 110. By maintaining sensor 130 at a constant distance from fastener 110 and maintaining excitation unit 120 substantially centered on fastener 110, there is no signal change due to the fastener boundary such as would occur if the sensor were moved across the boundary between the layers of object 199 and fastener 110. The sensor 130 is positioned so that it can be rotated around the excitation unit 120 and the fastener 110 to detect the presence of an anomaly 105 that is located below a fastener 110 included within the object 199.

Figure 9:
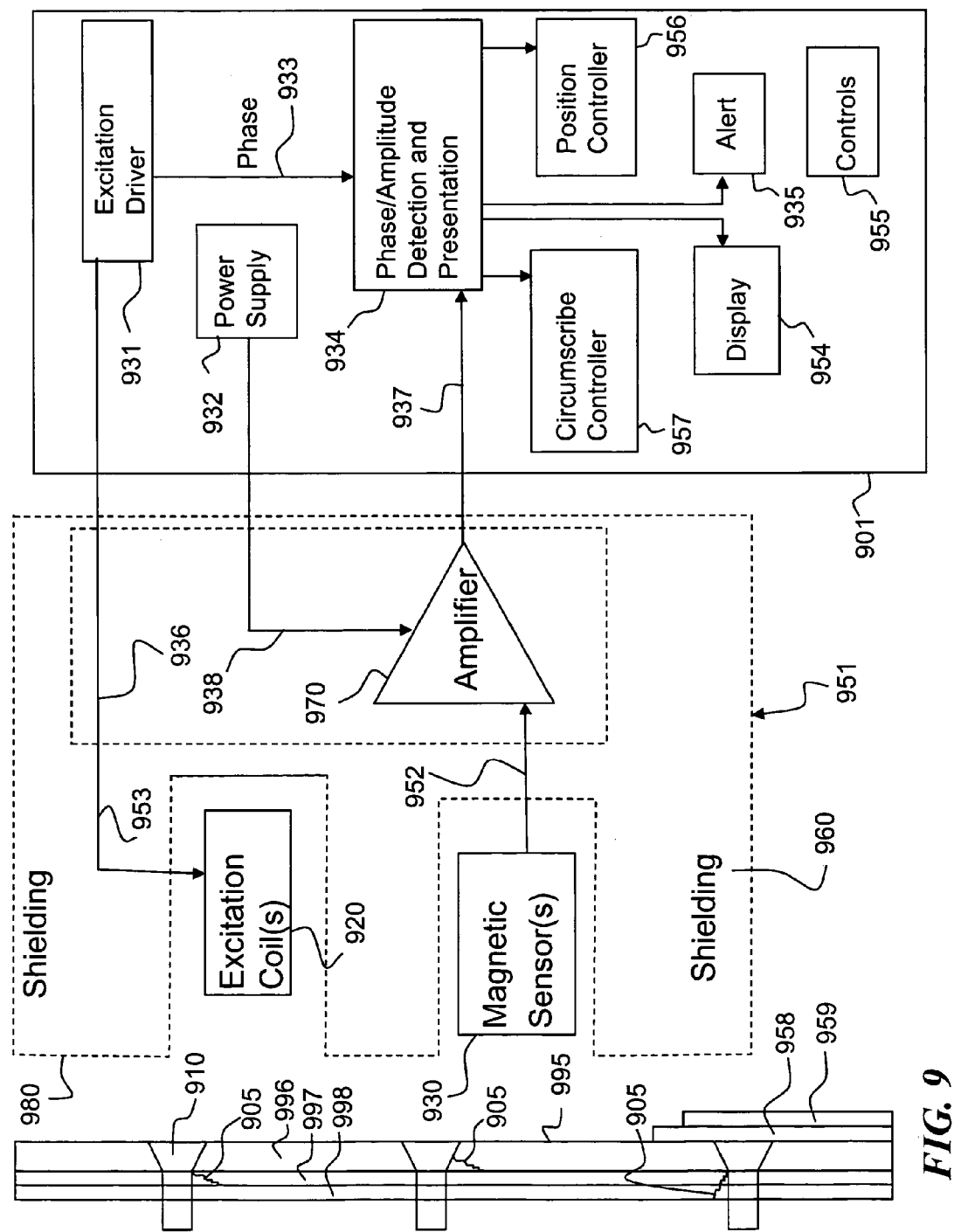
FIG. 9 is a block diagram of an apparatus 900 of the invention.

In some embodiments, this and each of the following probes are operatively coupled to an analysis and output system such as shown in FIG. 9 and described below. In some embodiments, the analysis and output system senses and/or controls the positioning and rotation of the probe, provides the excitation signal to drive excitation unit 120, and analyzes the phase and magnitude changes of the signal from sensor 130 in order to determine, and to provide an output indication of, the type, size, and/or location of anomaly or flaw 105. Accordingly, use of the apparatus 100 of the invention allows detection of the presence of an anomaly 105 that is hidden within object 199 and next to and/or below the fastener 110.

Figure 1B:
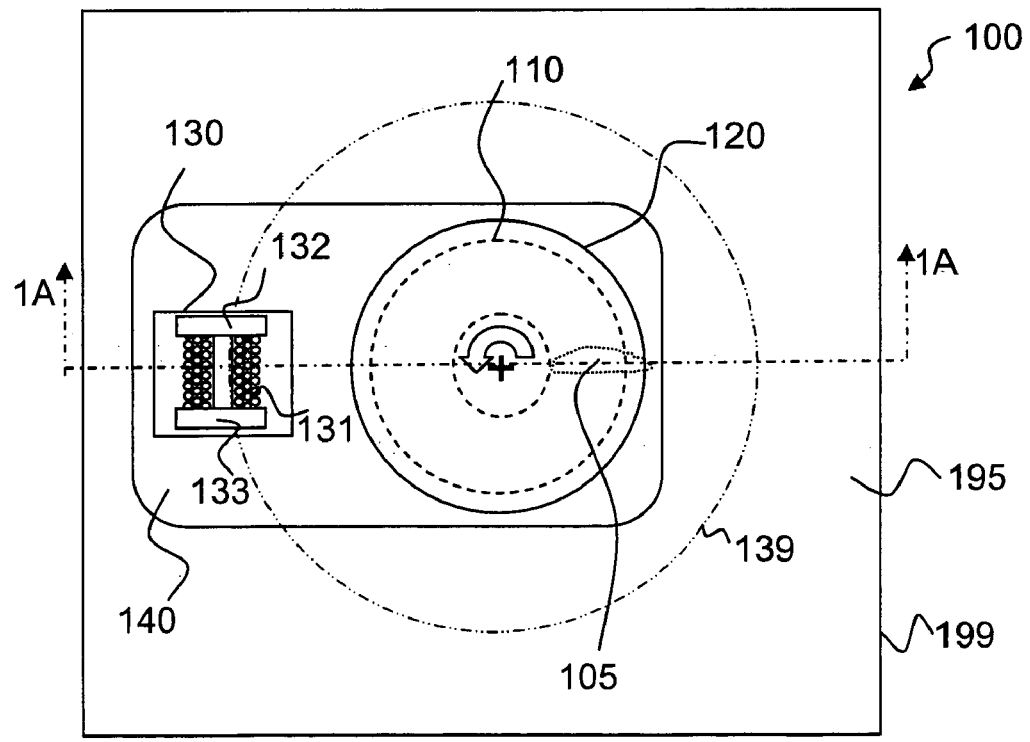
FIG. 1B is a top-view of apparatus 100 having a sensor that rotates around an excitation unit that is positioned over a structure that penetrates a surface of an object.

FIG. 1B is a top view of device 100, which is shown in side cross section in FIG. 1A. More specifically, FIG. 1B illustrates rotation of a sensor 130 along a path 139 around the excitation unit 120 of the apparatus 100 and a fastener 110 during scanning of the object for the presence of an anomaly 105 contained within the object 199. The excitation unit 120 is substantially centered on the fastener 110. In some embodiments, sensor 130 includes a core 131 that has its two poles 132 and 133 oriented along a tangent to a radial line from the center of fastener 110 in a differential sensing configuration In other embodiments, other sensor configurations, such as an absolute sensor (e.g., a vertical coil with a single vertical core) are used. When both poles 132 and 133 of core 131 in a differential sensing configuration are to one side of flaw 105 or on the opposite side of fastener 110 from flaw 105, the magnetic flux path through object 199 is uninterrupted and one type (i.e., magnitude and phase) of signal is received by sensor 130, but as sensor 130 is moved around the perimeter of fastener 110 such that pole 132 is on the opposite side of flaw 105 relative to pole 133, the flux path is changed such that a different type of signal is received by sensor 130 (i.e., the magnitude and/or phase changes relative to other positions of the sensor 130 relative to the flaw 105). Rotation of the sensor 130 around the fastener 110 allows the presence of an anomaly 105 located below and/or next to the fastener 110 to be detected.

Figure 1C:
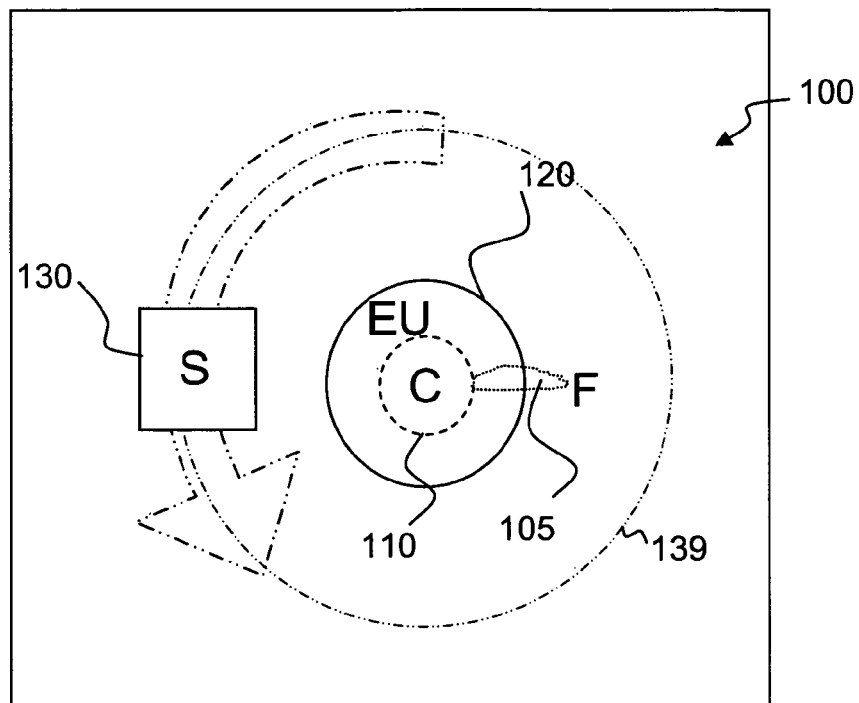
FIG. 1C is a schematic diagram illustrating the movement of a sensor (S) around an excitation unit (EU). (S) is a sensor, (EU) is an excitation unit, and (F) is a fastener.

FIG. 1C is a block diagram applicable to probe 100 of FIG. 1A, illustrating rotation of a sensor S 130 around a fastener 110 on which an excitation unit EU 120 is substantially centered C in order to detect the presence of an anomaly F 105 that has formed or developed under the fastener 110.

Figure 2C:
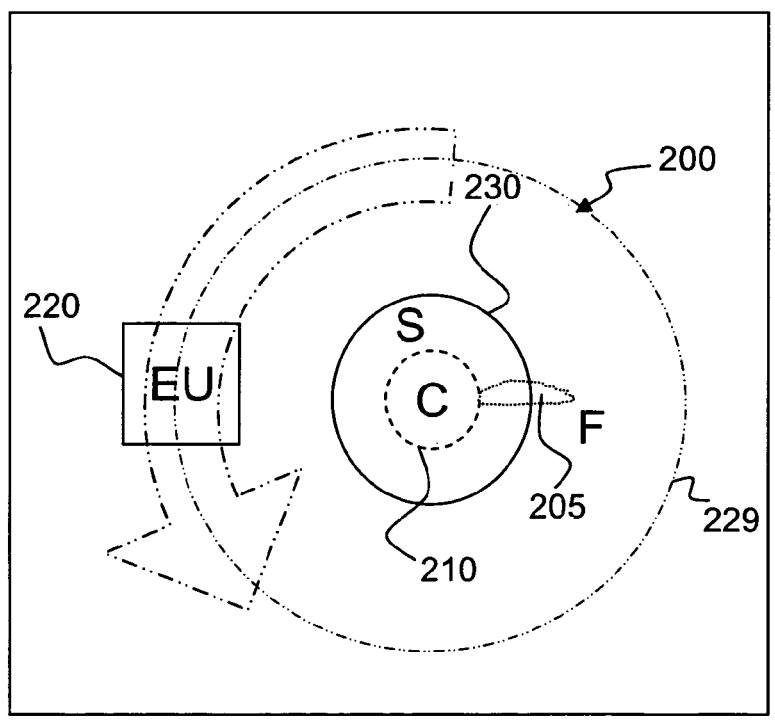
FIG. 2C is a schematic diagram illustrating the movement of an excitation unit (EU) around a sensor (S). (S) is a sensor, (EU) is an excitation unit, (F) is a fastener, and (C) is an anomaly.
Figure 2A:
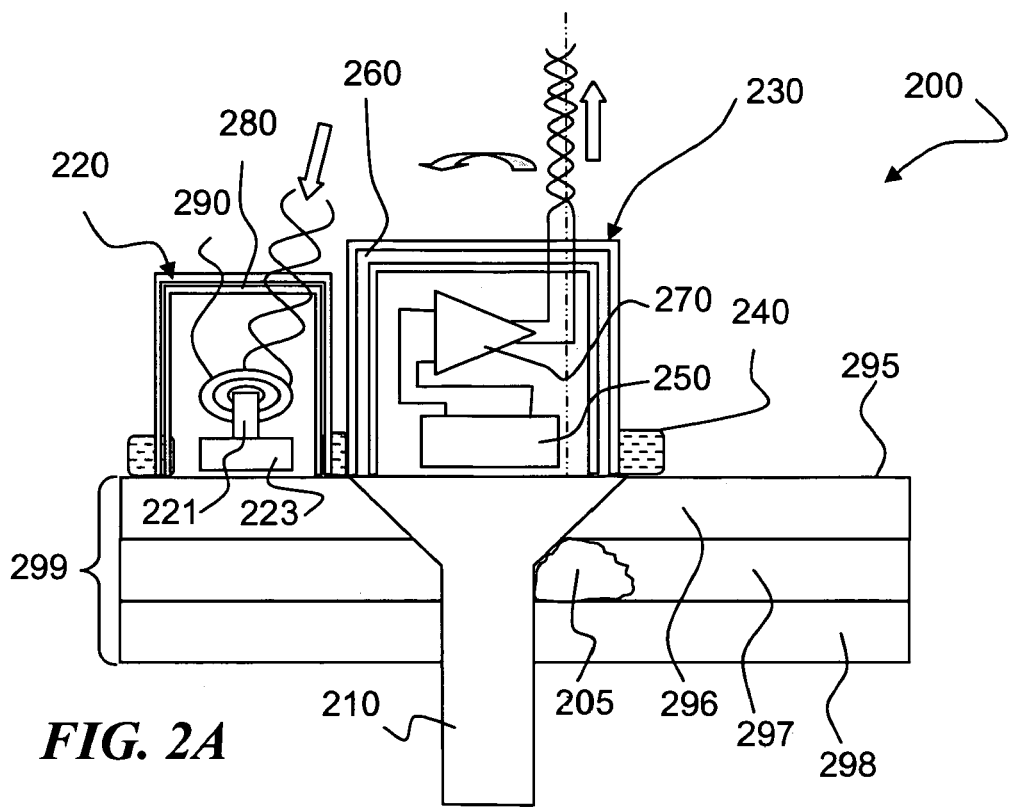
FIG. 2A is a side-view of an apparatus 200 having an excitation unit that is positioned to be rotated around a sensor that is positioned over a structure that penetrates a surface of an object.

FIG. 2A is a schematic side cross-section view (along cut line 2A of FIG. 2B) of an apparatus 200 of the invention that is positioned on the surface 295 of an object 299 that contains an anomaly 205. In some embodiments, object 299 includes a fastener 210 that penetrates multiple layers 296, 297 and 298 of the object 299. The apparatus 200 includes an excitation unit 220 and a sensor 230 configured to have excitation unit 220 moved along path 229 at a substantially constant distance from the edge of fastener 210. The excitation unit illustrated in FIG. 2A includes excitation coil 290 and excitation unit shielding 280, and, in some embodiments, a core 221 that has its two poles 222 and 223 oriented along a tangent to a radial line from the center of fastener 210 in a differential driving or excitation configuration. In other embodiments, other excitation unit configurations, such as an absolute excitation configuration (e.g., a vertical coil with a single vertical core, such as excitation unit 120 of FIG. 1A) is used. In still other embodiments, other configurations such as a set of coils driven to generate a traveling wave or rotating wave (e.g., see FIG. 6B and its description below). When both poles 222 and 223 of core 221 are to one side of flaw 205 or on the opposite side of fastener 210 from flaw 205, the magnetic flux path through object 299 is uninterrupted and one type (i.e., magnitude and phase) of signal is received by sensor 230, but as excitation unit 220 is moved around the perimeter of fastener 210 such that pole 222 is on the opposite side of flaw 205 relative to pole 223, the flux path is changed such that a different type of signal is received by sensor 230 (i.e., the magnitude and/or phase changes relative to other positions of the excitation unit 220 relative to the flaw 205). The sensor 230 illustrated in FIG. 2A includes an amplifier 270, a sensing coil or other magnetic sensor 250 and sensor shielding 260. A base 240, in some embodiments, is made of a dielectric material or magnetic shielding. In some embodiments, base 240 is configured to facilitate moving excitation unit 220 around a perimeter of fastener 110 while keeping centered sensor 230 on fastener 210. The sensor 230 is substantially centered over fastener 210. The excitation unit 220 is positioned so that it can be rotated along a path 239 around the sensor unit 230 and the fastener 210 to detect the presence of an anomaly 205 that is located below a fastener 210 included within the object 299. Accordingly, use of the apparatus 200 of the invention allows the presence of an anomaly 205 that is hidden below and/or next to the fastener 210 to be detected.

Figure 2B:
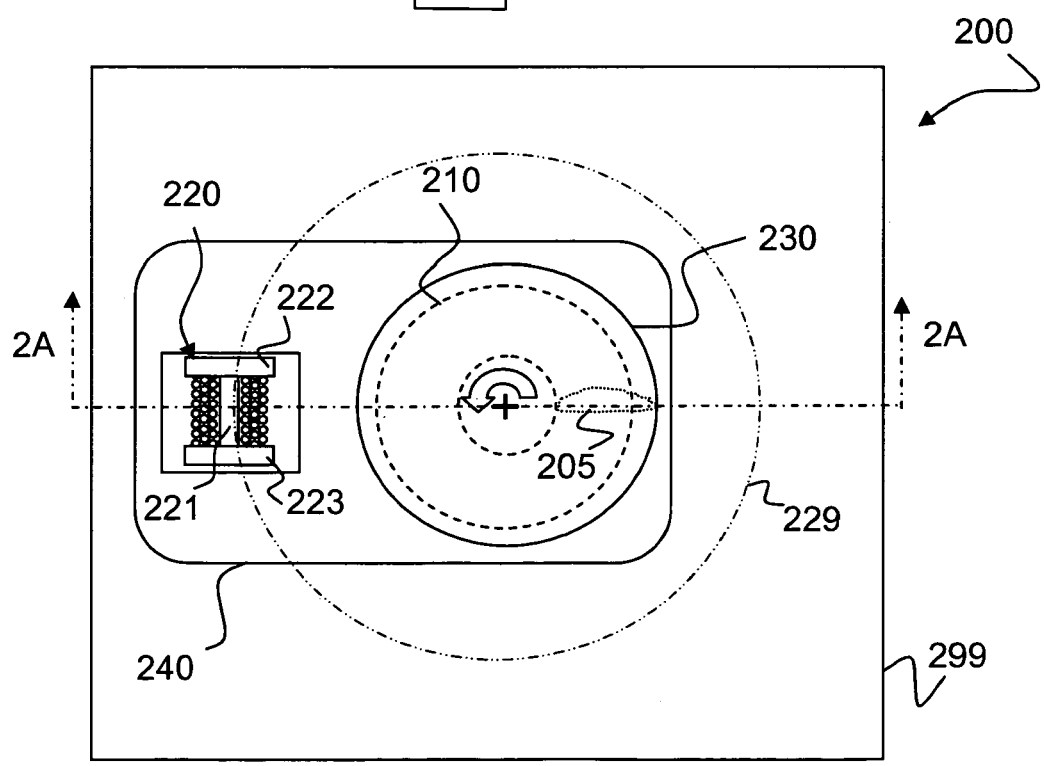
FIG. 2B is a top-view of apparatus 200 having an excitation unit that rotates around a sensor that is positioned over a structure that penetrates a surface of an object.

FIG. 2B is a top view of device 200, which is shown in side cross section in FIG. 2A. More specifically, FIG. 2B illustrates rotation of an excitation unit 220 around the sensor 230 of the apparatus 200 and a fastener 210 during scanning of the object for the presence of an anomaly 205 contained within the object 299. The sensor 230 is substantially centered on the fastener 210. Rotation of the excitation unit 220 around the fastener 210 allows the presence of an anomaly 205 located below and/or next to the fastener 210 to be detected.

FIG. 2C is a block diagram, applicable to probe 200 of FIG. 2A, illustrating rotation of an excitation unit EU 220 around a fastener 210 on which a sensor S 230 is substantially centered C in order to detect the presence of an anomaly F 205 that is positioned under the fastener 210.

Figure 3A:
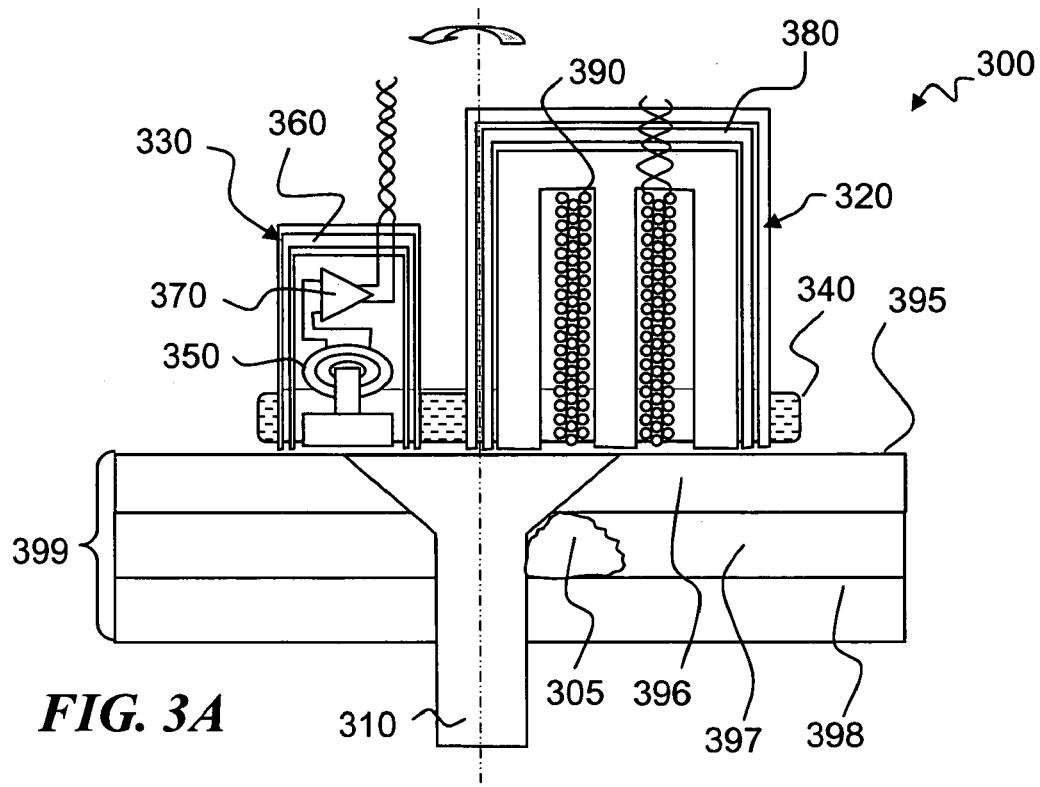
FIG. 3A is a side-view of an apparatus 300 having an excitation unit and a sensor that are positioned to be rotated around a structure that penetrates a surface of an object.

FIG. 3A is a schematic cross-sectional elevation side view (along section line 3A shown in FIG. 3B) that illustrates one embodiment of an apparatus or probe 300 of the invention, which is positioned on the surface 395 of an object 399 that contains an anomaly 305 (such as a small crack). The object 399 includes a fastener 310 that penetrates multiple layers 396, 397 and 398 of the object 399. The apparatus 300 includes an excitation unit 320 and a sensor 330. The excitation unit illustrated in FIG. 3A includes one excitation coil 390 and excitation unit shielding 380. The sensor 330 illustrated in FIG. 3A includes an amplifier 370, a coil 350 and sensor shielding 360. A base 340, in some embodiments, is made of a dielectric material and/or magnetic shielding, and connects excitation unit 320 and sensor 330. The excitation unit 320 and the excitation unit 320 are positioned so that neither is centered over the fastener 310. The sensor 330 and the excitation unit 320 are positioned so that they can be rotated along a path 329 with a substantially constant distance from the fastener 310 to detect the presence of an anomaly 305 that is located below the fastener 310 included within the object 399. In some embodiments, a sharp protrusion or a suction cup or other mechanism on base 340 is affixed relative to the fastener's center point 349, in order to allow the probe 300 to be rotated around point 349 keeping excitation unit 320 and sensor 330 each at their own respective constant distance from path 329 or from the perimeter of fastener 310. Accordingly, use of the apparatus 300 of the invention allows the presence of an anomaly 305 that is hidden below and/or next to the fastener 310 to be detected.

Figure 3B:
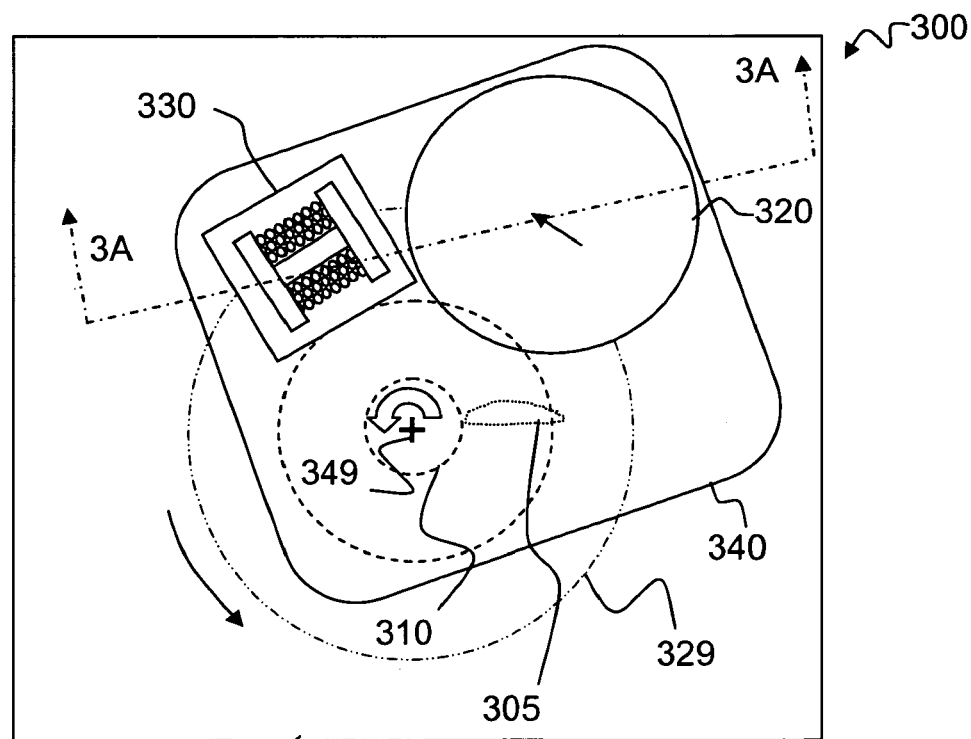
FIG. 3B is a top-view of apparatus 300 having an excitation unit and a sensor that both rotate around a structure on a surface of an object.

FIG. 3B is a top view of device 300, which is shown in side cross section in FIG. 3A. More specifically, FIG. 3B illustrates rotation of a sensor 330 and an excitation unit 320 of the apparatus 100 around a fastener 310 during scanning of the object for the presence of an anomaly 305 contained within the object 399. The excitation unit 320 and the sensor 330 are positioned so that neither is substantially centered on the fastener 310. Rotation of the sensor 330 and the excitation unit 320 around the fastener 310 allows the presence of an anomaly 305 located below and/or next to the fastener 310 to be detected.

Figure 3C:
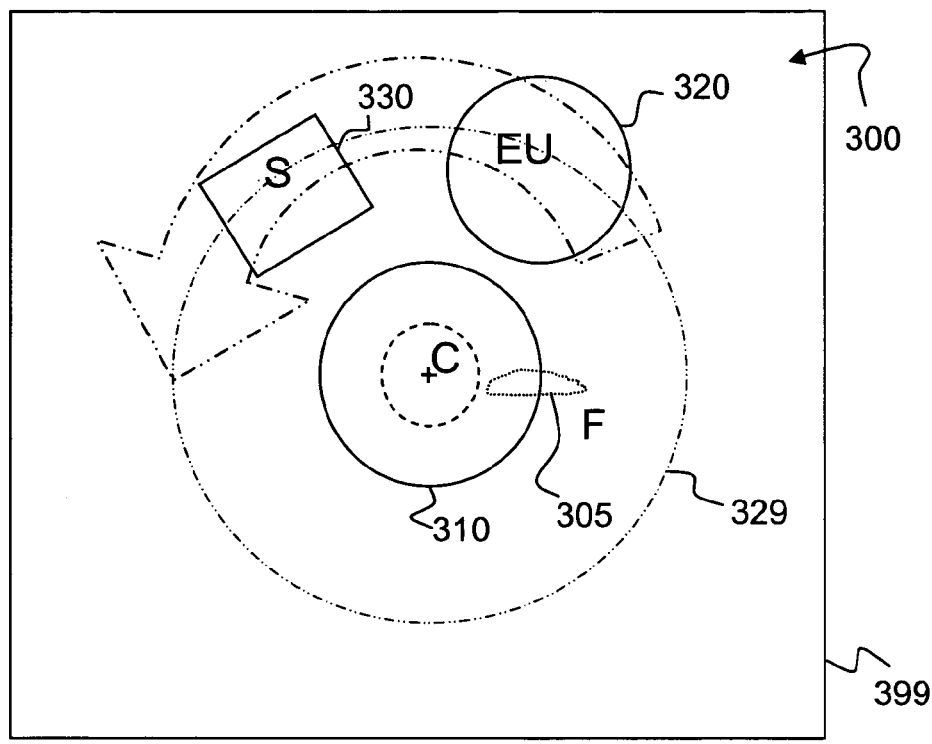
FIG. 3C is a schematic diagram illustrating the movement of excitation unit (EU) 320 and sensor (S) 330 around structure 310 on surface 399. (S) is a sensor, (EU) is an excitation unit, (F) is a fastener, and (C) is an anomaly.

FIG. 3C is a block diagram applicable to probe 300 of FIG. 3A, illustrating rotation of a sensor 330 and an excitation unit 320 around a fastener 310 in order to detect the presence of an anomaly 305 that is positioned under the fastener 310.

Figure 4C:
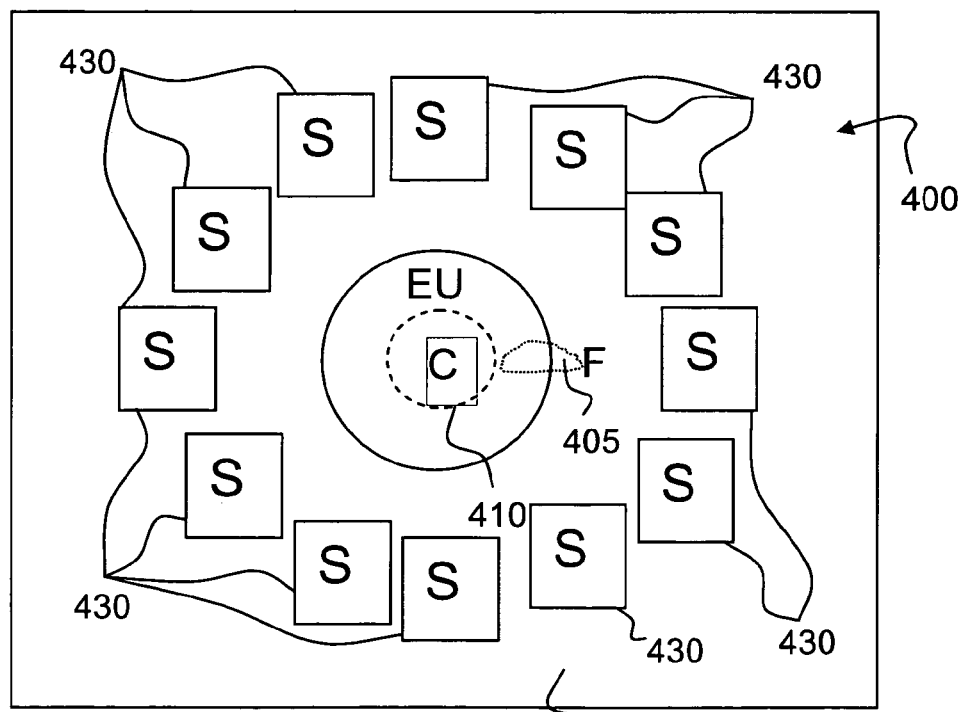
FIG. 4C is a schematic diagram illustrating the position of an excitation unit (EU) 420 and a plurality of sensors (S) 430 that are substantially centered on structure 410 on a surface 499. Each (S) is a sensor, (EU) is an excitation unit, (F) is a fastener, and (C) is an anomaly.
Figure 4A:
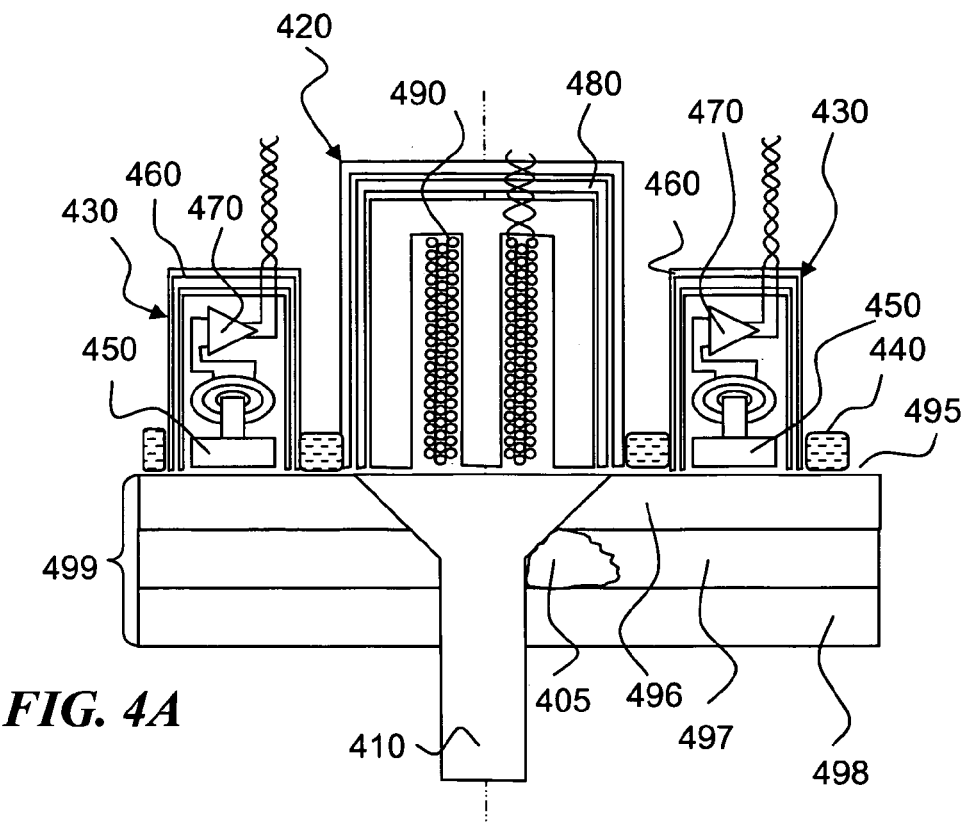
FIG. 4A is a side-view of an apparatus 400 having an excitation unit and a plurality of sensors that is substantially centered over a structure that penetrates a surface of an object.

FIG. 4A is a cross-sectional side view (along section line 4A shown in FIG. 4B) that illustrates one embodiment of an apparatus or probe 400 of the invention. Probe 400 is positioned on the surface 495 of an object 499 that contains an anomaly 405. The object 499 includes a fastener 410 that penetrates multiple layers 496, 497 and 498 of the object 499. The apparatus 400 includes an excitation unit 420 and a plurality of sensors 430. The excitation unit illustrated in FIG. 4A includes one excitation coil 490 and excitation unit shielding 480. Each of the sensors 430 illustrated in FIG. 4A includes an amplifier 470, a coil 450 and sensor shielding 460. In some embodiments, a base 440 (made of e.g., a dielectric material and/or magnetic shielding) is provided and connects excitation unit 420 and sensor 430. The excitation unit 420 is substantially centered over the fastener 410. The analysis electronics (see FIG. 9) simultaneously or sequentially examines the signals from each of the sensors without moving probe 400. The plurality of sensors 430 are positioned around the excitation unit 420 and the fastener 410 to detect the presence of an anomaly 405 that is located below and/or next to fastener 410 without needing to move probe 400. The differences between the different sensor signals of a stationary probe 400 can be analyzed to determine the location of flaw 405 in much the same way as is done by analyzing the signal differences obtained at different orientations caused by moving probe 100 (FIG. 1) around a periphery of an anomaly. In other embodiments, probe 400 can be used in a moving mode wherein the angle of movement is smaller than would otherwise be needed (i.e., a probe 400 having 12 sensors needs only be moved across a 30-degree angle, whereas probe 100 might need to be moves across a 360-degree angle, thus using electronics processing to speed up the overall inspection process. Accordingly, use of the apparatus 400 with its plurality of sensors 430 of the invention allows the presence of an anomaly 405 that is hidden below and/or next to the fastener 410 to be detected.

Figure 4B:
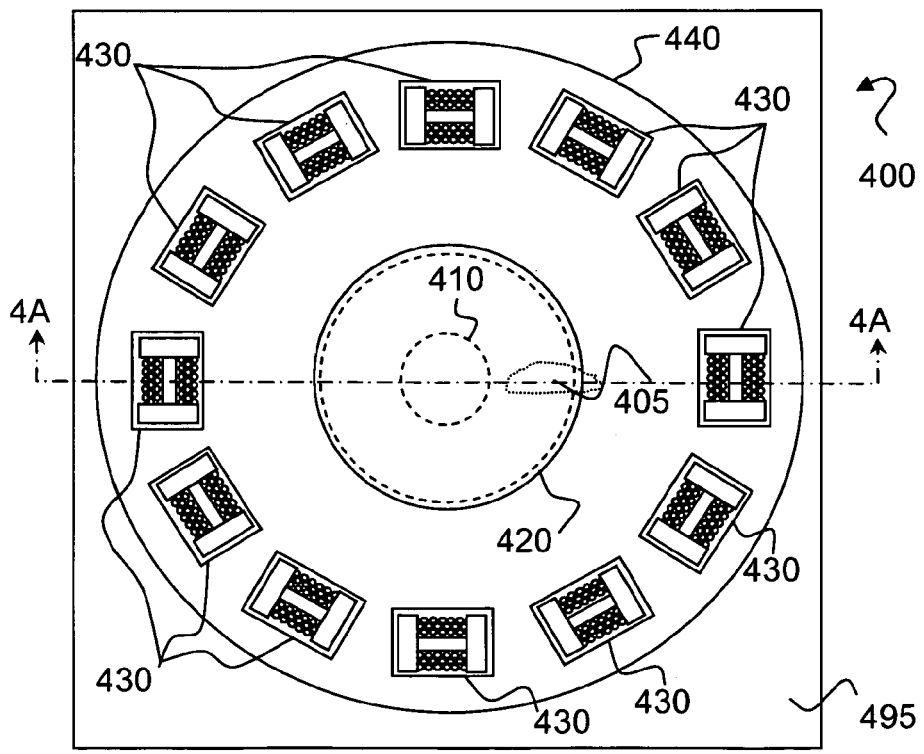
FIG. 4B is a top-view of apparatus 400 having an excitation unit and a plurality of sensors that is substantially centered over a structure on a surface of an object.

FIG. 4B is a top view of device 400, which is shown in side cross section in FIG. 4A. More specifically, FIG. 4B illustrates a plurality of sensors 430 that are positioned around the excitation unit 420 of the apparatus 400 and a fastener 410 during scanning of the object for the presence of an anomaly 405 contained within the object 499. The excitation unit 420 is maintained substantially centered on the fastener 410. The plurality of sensors 430 around the fastener 410 allow the presence of an anomaly 405 located below and/or next to the fastener 410 to be detected without moving probe 400 or moving it only slightly.

FIG. 4C is a block diagram, applicable to probe 400 of FIG. 4A, illustrating a plurality of sensors 430 that are positioned around a fastener 410 on which an excitation unit 420 is substantially centered in order to detect the presence of an anomaly 405 that is positioned under the fastener 410.

Figure 5A:
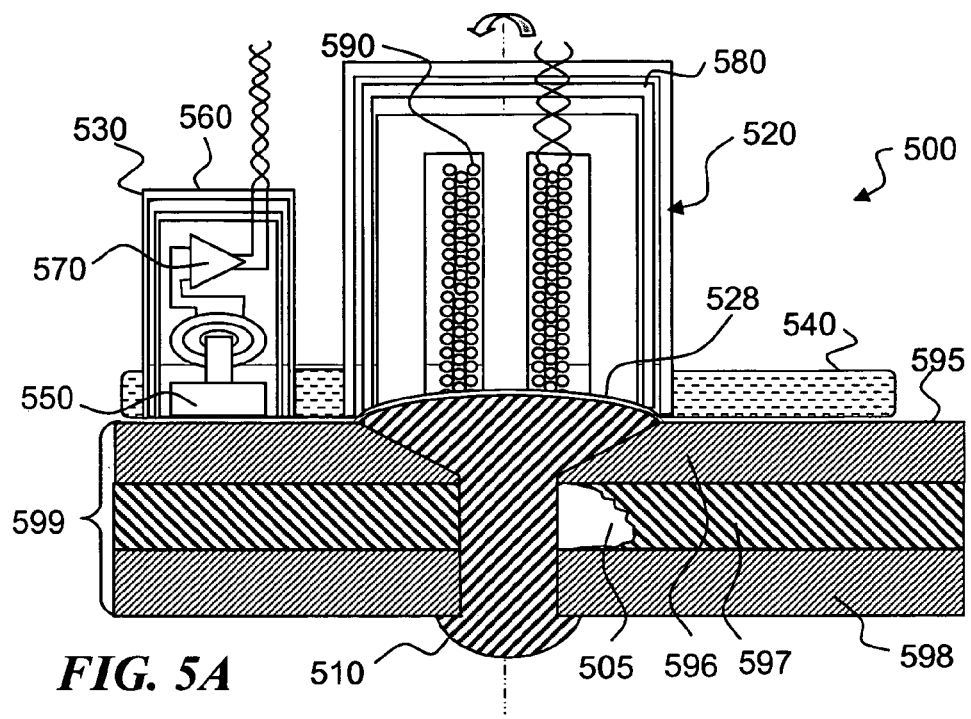
FIG. 5A is a side-view of an apparatus 500 having a sensor 530 that is positioned to be rotated around an excitation unit 520 having an indentation that is substantially centered over a raised structure 510 that penetrates a surface of an object.

FIG. 5A is a cross-sectional elevation side view (along section line 5A shown in FIG. 5B) that illustrates one embodiment of an apparatus or probe 500 of the invention. Probe 500 is substantially the same as probe 100 of FIG. 1A and FIG. 1B, except that probe 500 includes a dimple or indentation 528 under excitation unit 520 that has a size and shape to fit (e.g., with sufficient snugness to allow rotation of probe 500 at a desired degree of precision) on the raised head of fastener (e.g., rivet) 510. Probe 500 is positioned on the surface 595 of an object 599 that contains an anomaly 505. In some embodiments, object 599 includes a fastener 510 that penetrates multiple layers 596, 597 and 598 of the object 599. In some embodiments, apparatus 500 includes an excitation unit 520 and a one or more sensors 530. The excitation unit illustrated in FIG. 5A includes excitation coil 590 and excitation unit shielding 580. In some embodiments, sensor 530 illustrated in FIG. 5A includes an amplifier 570, a coil 550 and sensor shielding 560. In some embodiments, a base 540 (made of e.g., a dielectric material and/or magnetic shielding) is provided and connects excitation unit 520 and sensors 530. The excitation unit 520 is substantially centered over fastener 510. The sensor 530 is positioned so that it can be rotated around the excitation unit 520 and the fastener 510 to detect the presence of an anomaly 505 that is located below and/or next to a fastener 510 included within the object 599. Accordingly, use of the apparatus 500 of the invention allows the presence of an anomaly 505 that is hidden below the fastener 510 to be detected.

Figure 5B:
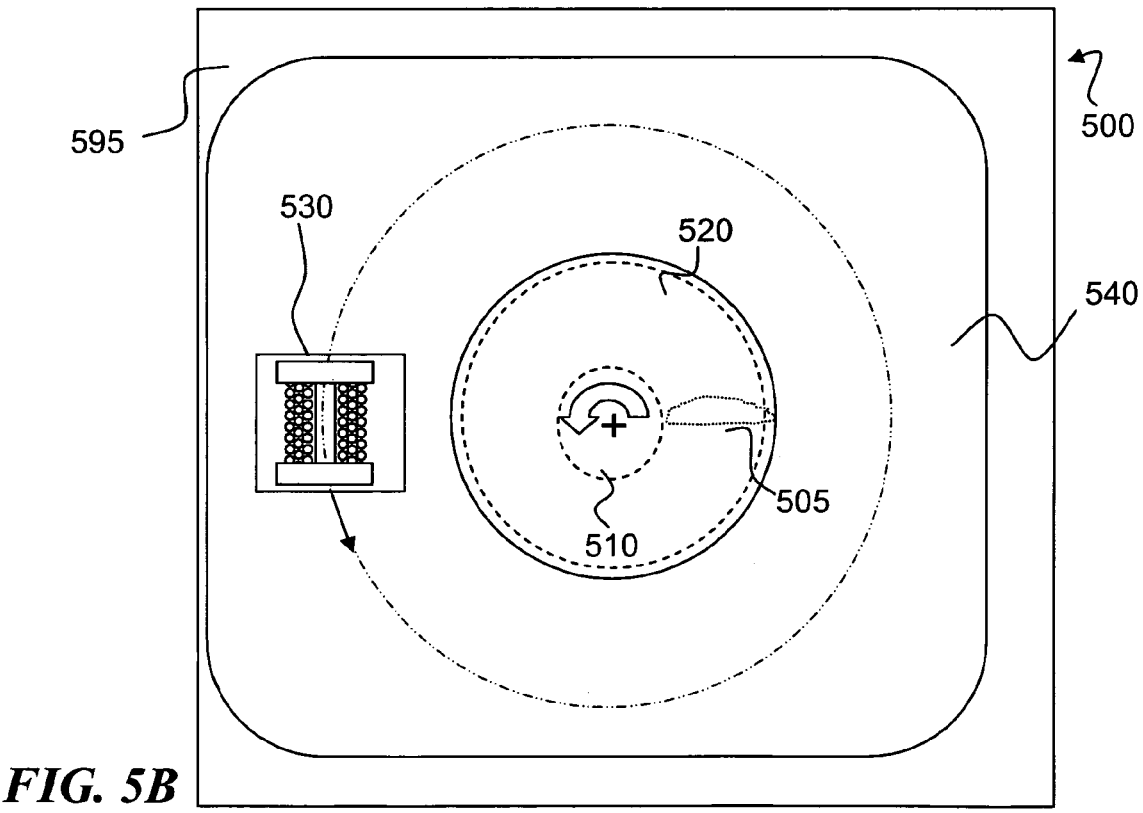
FIG. 5B is a top-view of apparatus 500 having a sensor that rotates around an excitation unit that is substantially centered over a structure that penetrates a surface of an object.

FIG. 5B is a top view of device 500, which is shown in side cross section in FIG. 5A. More specifically, FIG. 5B illustrates rotation of a sensor 530 around the excitation unit 520 of the apparatus 500 and a fastener 510 during scanning of the object for the presence of an anomaly 505 contained within the object 599. The excitation unit 520 is substantially centered on the fastener 510. Rotation of the sensor 530 around the fastener 510 allows the presence of an anomaly 505 located below and/or next to the fastener 510 to be detected.

Figure 5C:
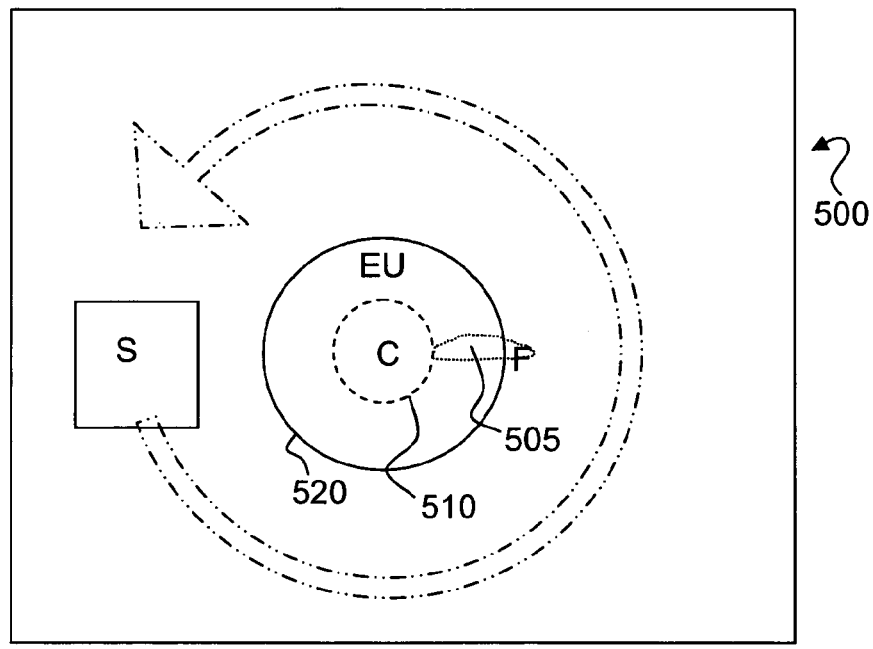
FIG. 5C is a schematic diagram illustrating the movement of a sensor (S) 530 around an excitation unit (EU) 520. (S) is a sensor, (EU) is an excitation unit, (F) is a fastener, and (C) is an anomaly.
Figure 5D:
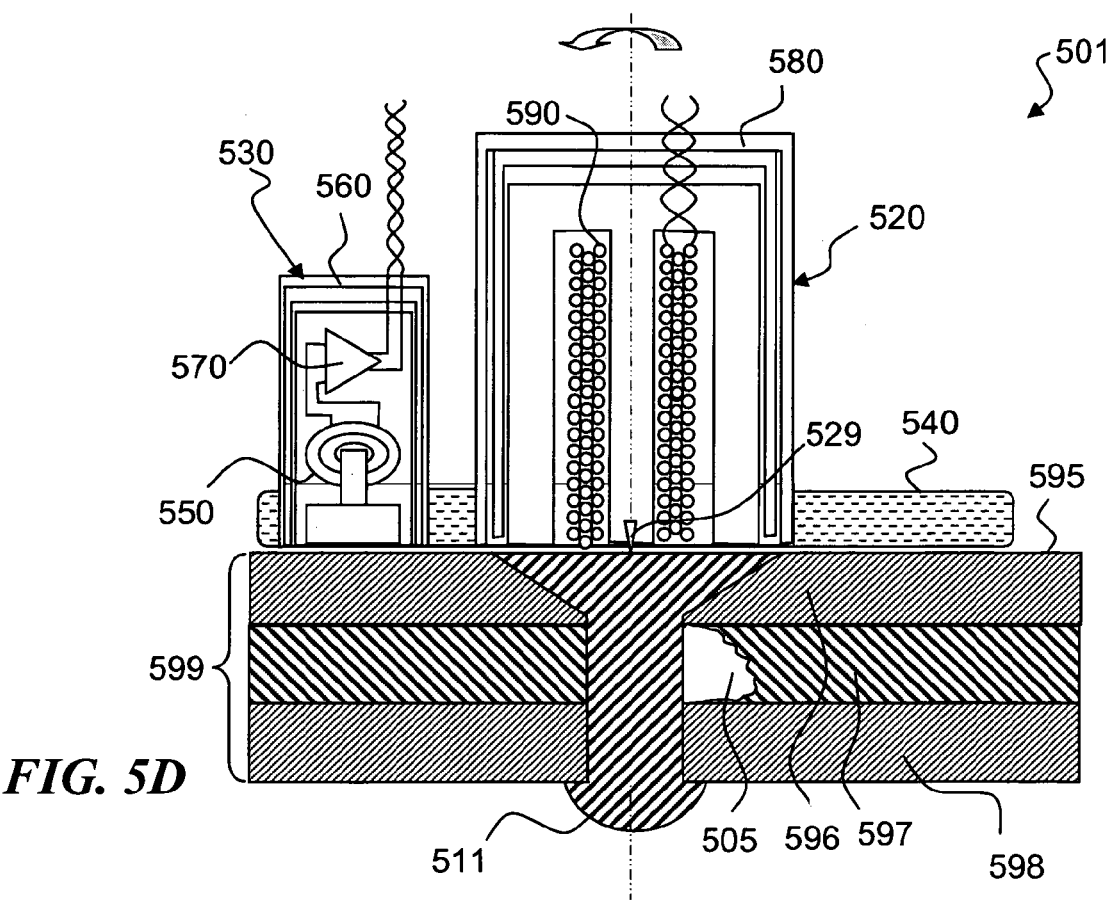
FIG. 5D is a side-view of an apparatus 501 having a sensor 530 that is positioned to be rotated around an excitation unit 520 having a sharp protrusion to center over a flat-topped structure 511 that penetrates a surface of an object.

FIG. 5C is a schematic, applicable to probe 500 of FIG. 5A or probe 501 of FIG. 5D, illustrating rotation of a sensor 530 around a fastener 510 on which an excitation unit 520 is substantially centered in order to detect the presence of an anomaly 505 that is positioned under the fastener 510.

FIG. 5D is a cross-sectional elevation side view (along section line 5A shown in FIG. 5B) that illustrates one embodiment of an apparatus or probe 501 of the invention. Probe 501 is substantially the same as probe 100 of FIG. 1A and FIG. 1B, except that probe 500 includes a sharp protrusion 529 under excitation unit 520 that has a size and shape to slightly dent the flush head of (or fit into a dimple in) fastener (e.g., rivet) 511. Sharp protrusion 529 provides a point around which probe 501 is rotated. Other aspects and reference numbers of probe 501 are identical to probe 500 described above.

In some embodiments, probe 500 of FIG. 5A also includes a sharp protrusion 529 inside dimple 528 to provide a better grip on rivet 510 around which to pivot.

Figure 6A:
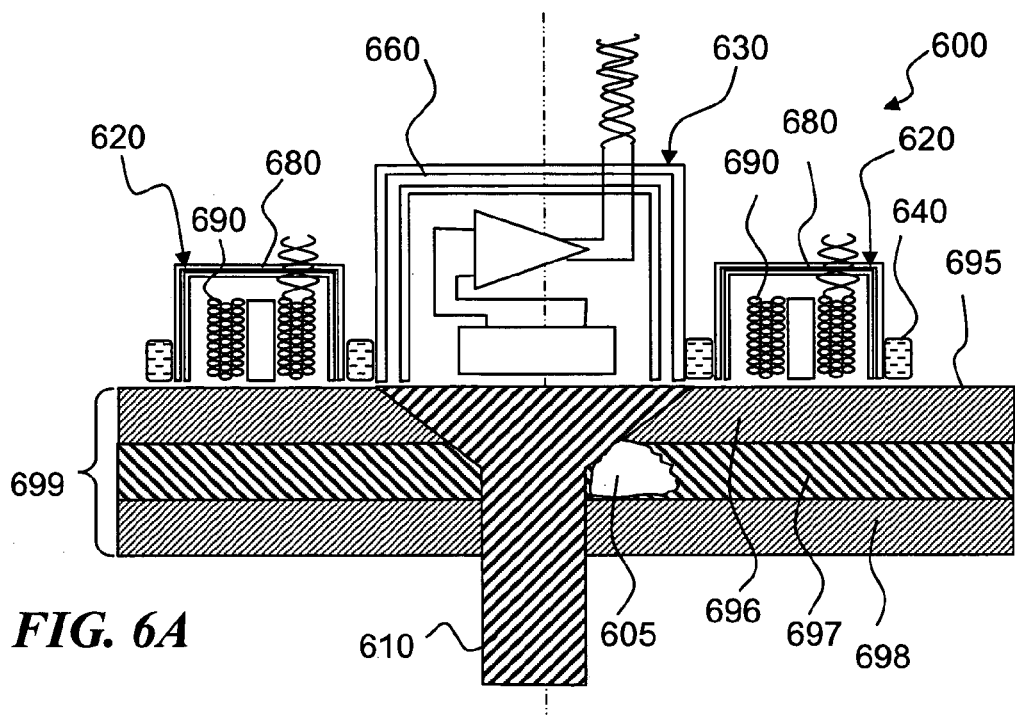
FIG. 6A is a side-view of an apparatus 600 having a sensor 630 and a plurality of excitation units 520, wherein the probe is substantially centered over a structure that penetrates a surface of an object.

FIG. 6A is a cross-sectional elevation side view (along section line 6A shown in FIG. 6B) that illustrates one embodiment of an apparatus or probe 600 of the invention. Probe 600 is positioned on the surface 695 of an object 699 that contains an anomaly 605. The object 699 includes a fastener 610 that penetrates multiple layers 696, 697 and 698 of the object 699. The apparatus 600 includes a sensor 630 and a plurality of excitation units 620 mounted on a support or base 640. The excitation units illustrated in FIG. 6A include plural excitation coils 690 and excitation unit shielding 680. The sensor 630 illustrated in FIG. 6A includes an amplifier 670, a coil 650 and sensor shielding 660. One or more sensors 630 are substantially centered over or around fastener 610. The plurality of excitation units 620 are positioned around sensor 630 and the fastener 610 to detect the presence of an anomaly 605 that is located below the fastener 610 included within the object 699. In some embodiments, the plurality of excitation units 620 are driven by a multi-phase excitation signal (e.g., from a control unit such as shown in FIG. 9 and described below) to generate a circularly rotating traveling wave (as described above and in U.S. Pat. No. 6,636,037) that moves around path 629 (see FIG. 6B). Accordingly, use of the apparatus 600 of the invention allows the presence of an anomaly 605 that is hidden below the fastener 610 to be detected. This embodiment of the invention can be used to generate a rotating magnetic field to detect an anomaly 605 within the object 699 being scanned.

Figure 6B:
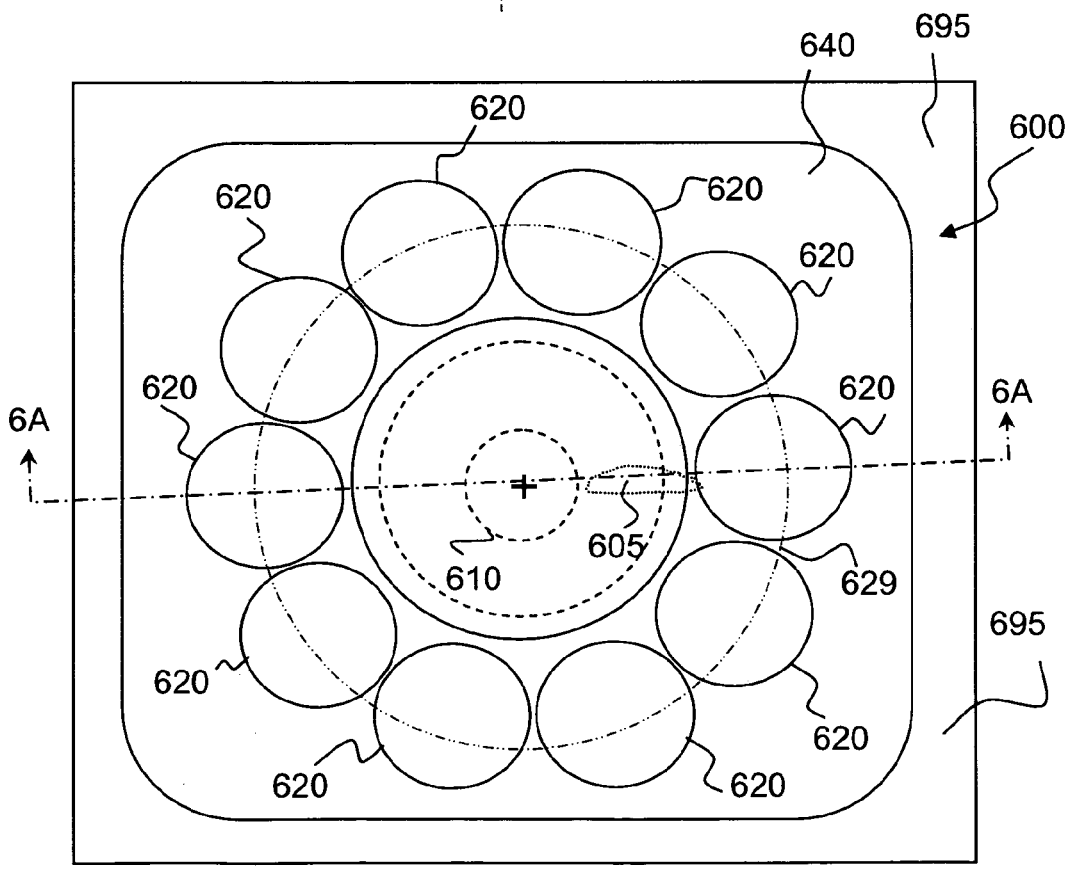
FIG. 6B is a top-view of apparatus 600 having a sensor and a plurality of excitation units that is substantially centered over a structure on a surface.

FIG. 6B is a top view of device 600, which is shown in side cross section in FIG. 6A. FIG. 6B illustrates the plurality of excitation units 620 that are positioned around the sensor 630 of the apparatus 600 and a fastener 610 during scanning of the object for the presence of an anomaly 605 contained within the object 699. The sensor 630 is substantially centered on the fastener 610. The plurality of excitation units 620 around the fastener 610 allow the presence of an anomaly 605 located below the fastener 610 to be detected.

Figure 6C:
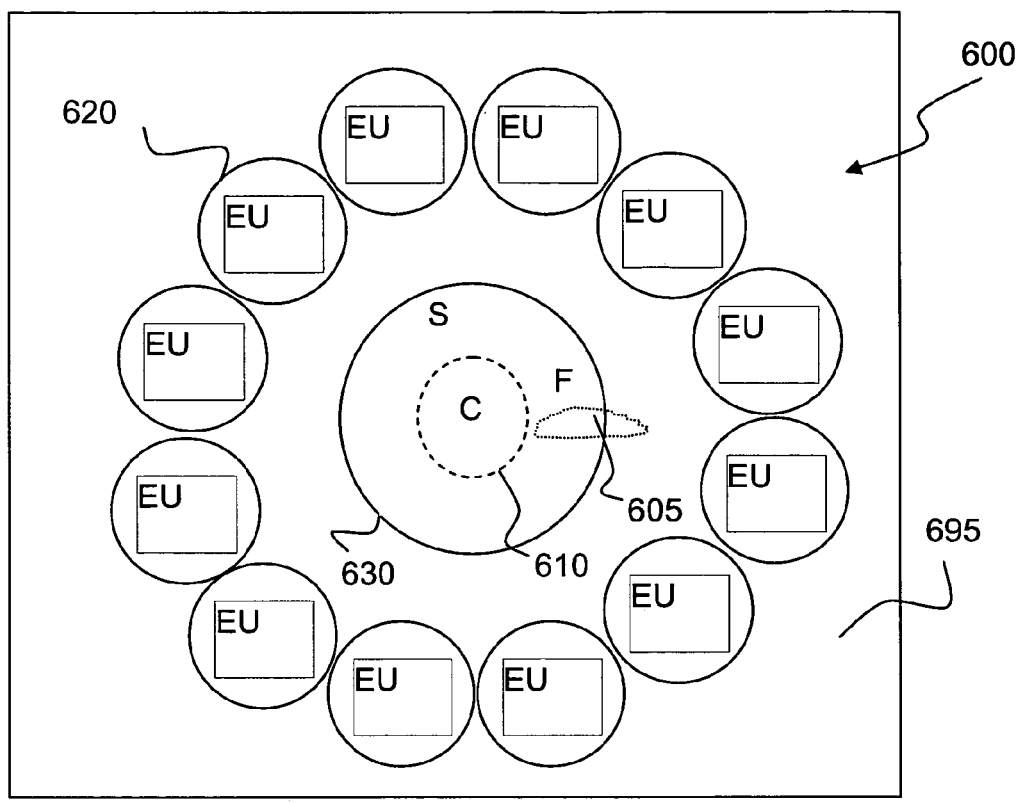
FIG. 6C is a schematic diagram illustrating the position of a sensor (S) and a plurality of excitation units (EU) that are substantially centered over a structure on a surface. (S) is a sensor, (EU) is an excitation unit, (F) is a fastener, and (C) is an anomaly.

FIG. 6C is a schematic, applicable to probe 600 of FIG. 6A, illustrating a plurality of excitation units 620 that are positioned around a fastener 610 on which a sensor 630 is substantially centered in order to detect the presence of an anomaly 605 that is positioned under the fastener 610.

Figure 6D:
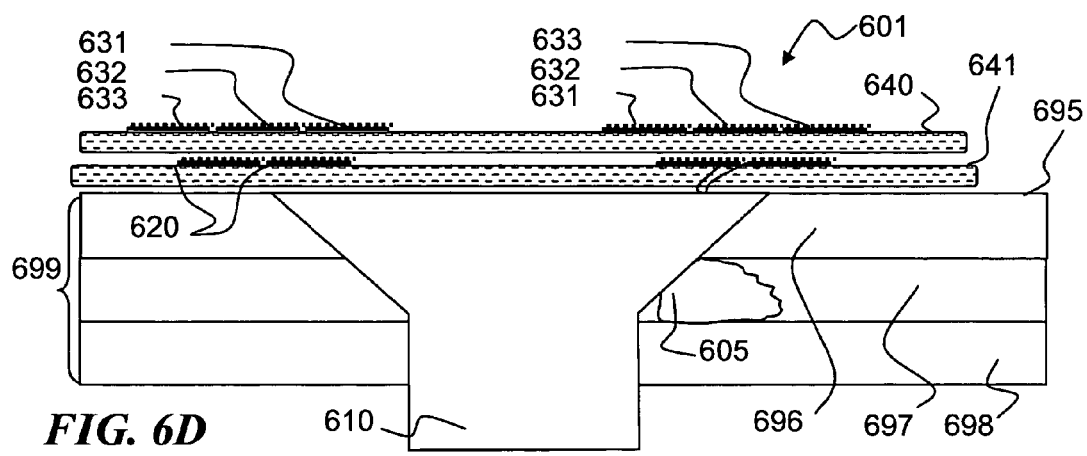
FIG. 6D is a side-view schematic diagram of a probe apparatus 601 having a plurality of sensors and a plurality of excitation units laid on a portion of surface 695.

FIG. 6D is a side-view schematic of apparatus 601 having a plurality of sensors 631, 632, and 633, and a plurality of excitation units 621 and 622, that substantially cover a portion of surface 695. Please note that the plurality of sensors 631, 632, and 633 are similar to sensors 430 of FIG. 4B, since as with FIG. 4B, there are a plurality (i.e., at least a subset) of the sensors 631, 632, and/or 633 arranged in a pattern (such as a circle) such that the controller 901 can read those sensors to obtain RFEC or eddy-current field readings around the periphery of fastener 610. In some embodiments, probe 601 is a combination of the configurations of FIGS. 6A, 6B, and 6C with the configurations of FIGS. 4A, 4B, and 4C is provided, thus providing an array or grid having a plurality of sensors 631, 632, and/or 633 arranged in three concentric circular rows, interspersed among or overlaid upon an array or grid having a plurality of excitation units 621 and/or 622. In some embodiments, the plurality of excitation units 621 and 622 and the plurality of 631, 632, and 633 are formed as spiral coils on one or on different layers of a thin flexible substrate 640 and/or 641 (which, in some embodiments, are laminated together) that can be laid across an object surface 695, even if the surface 695 is curved, convex, or concave. The number of, and the positioning of, the excitation units 620 and the number and positioning of the sensors 631, 632, and/or 633 are large enough and at a fine-enough granularity (i.e., many more coils that are each much smaller relative to the fastener than is shown in FIG. 6D) that the boundary between fastener 610 and object 699 can be followed (e.g., by driving and sensing the appropriate subsets of the EU and S coils) with enough precision to follow the outer boundary or contour of fastener 610. In some embodiments, the sensor coils 631, 632, and/or 633 and the excitation-unit coils 621 and/or 622 are arranged around the fastener 610 in one, two, three, or any other number of circles (or other shape chosen to allow following of the boundary of any particular fastener). In some embodiments, sensor coils 631, 632, and/or 633 are formed on one layer and the excitation-unit coils 621 and/or 622 are formed on a second layer, the two layers lying on top of each other. In some embodiments, the excitation-unit coils 621 and/or 622 are driven to globally generate a uniform AC magnetic field over at least some portion of the sensor array. In some embodiments, the excitation-unit coils 621 and/or 622 are driven to generating a traveling/rotating magnetic field over the sensor array. In some embodiments, a controller (such as Eddyscope 901 described below) is used to send a drive signal (or one or more phases of a drive signal) to a selected one or more of the plurality of excitation units 621 and/or 622, and to receive a signal from a selected one or more of the plurality of sensors 631, 632, and/or 633, in order to locate rivet 610 without moving apparatus 601. In other embodiments, the flex probe 601 is configured to be physically rotated over structure 610 (or rotated within a structure having a cavity or opening, such as structure 1010 described below and shown in FIG. 10A).

Figure 6E:
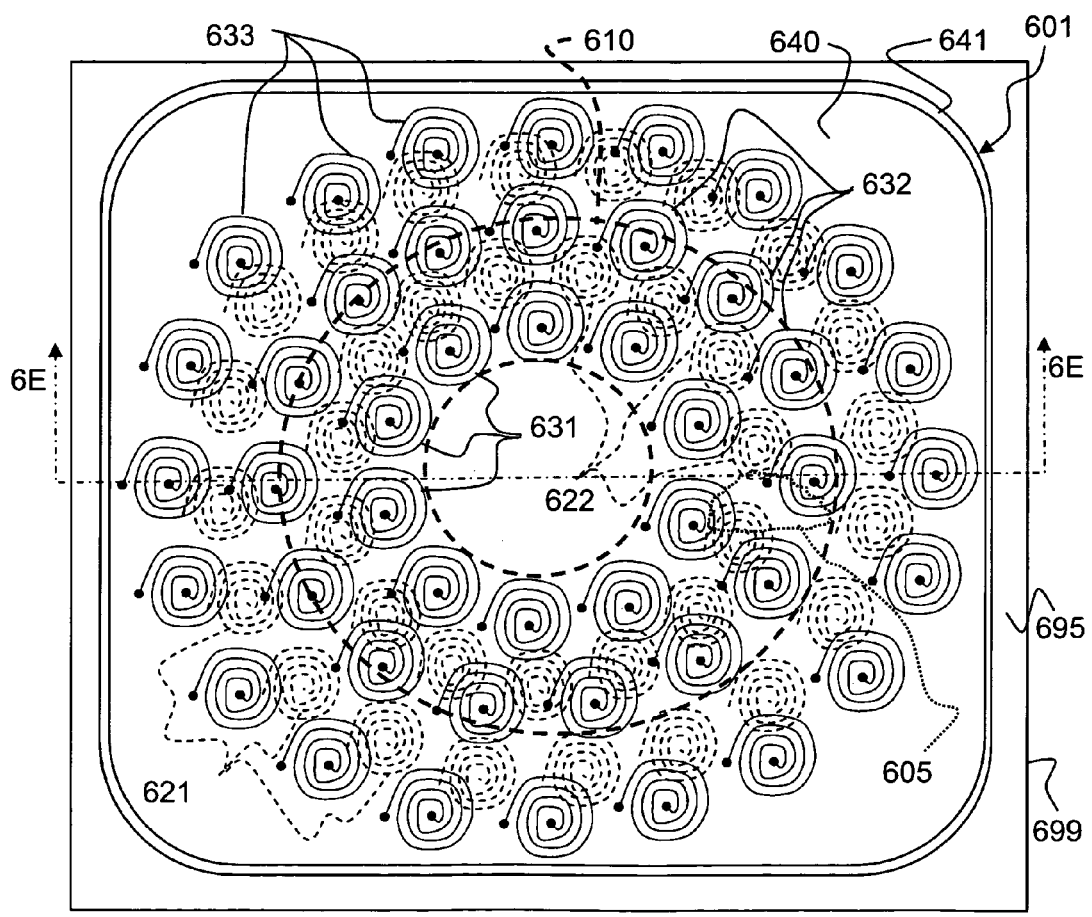
FIG. 6E is a top-view of apparatus 601 having a plurality of sensors and a plurality of excitation units that substantially cover a portion of surface 695.

FIG. 6E is a top-view of apparatus 601 having a sensor and a plurality of excitation units that is substantially centered over a structure on a surface. The controller (such as Eddyscope 901 described below) is then used to send a drive signal (or one or more phases of a drive signal) to each of one or more of the plurality of excitation units 621 (and/or 622) on or surrounding rivet 610, and to receive a signal from one or more of the plurality of sensors 633 (and/or 632 and/or 631), in order to locate flaw 605 next to or under rivet 610 without moving apparatus 601.

Figure 6F:
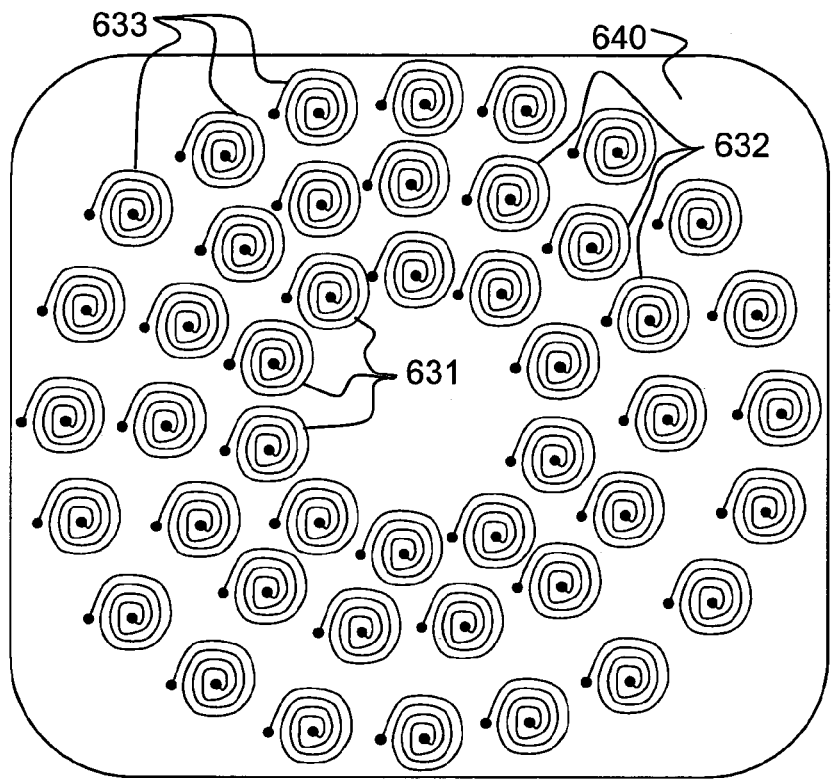
FIG. 6F is a top-view of flex substrate 640 having a plurality of sensors 631, 632, and 633.

FIG. 6F is a top-view of flex substrate 640 having a plurality of sensors 631, 632, and 633 arranged in three concentric circular rows. In some embodiments, the outer row of sensors 633 are used for fasteners having larger circular boundaries, the middle row of sensors 632 are used for fasteners having medium-sized circular boundaries, and the inner row of sensors 631 are used for fasteners having small circular boundaries. In other embodiments, one or more different row selections are used for the various-sized fasteners. In yet other embodiments, other numbers of sensors, other numbers of rows, or other patterns of sensors (such as a Cartesian arrangement of rows and columns) and the desired subsets of sensors are selected (e.g., a circular-row pattern of coils selected from a larger set of sensor coils on substrate 640) and used to achieve the desired sense scanning along an arbitrarily-shaped or sized boundary.

Figure 6G:
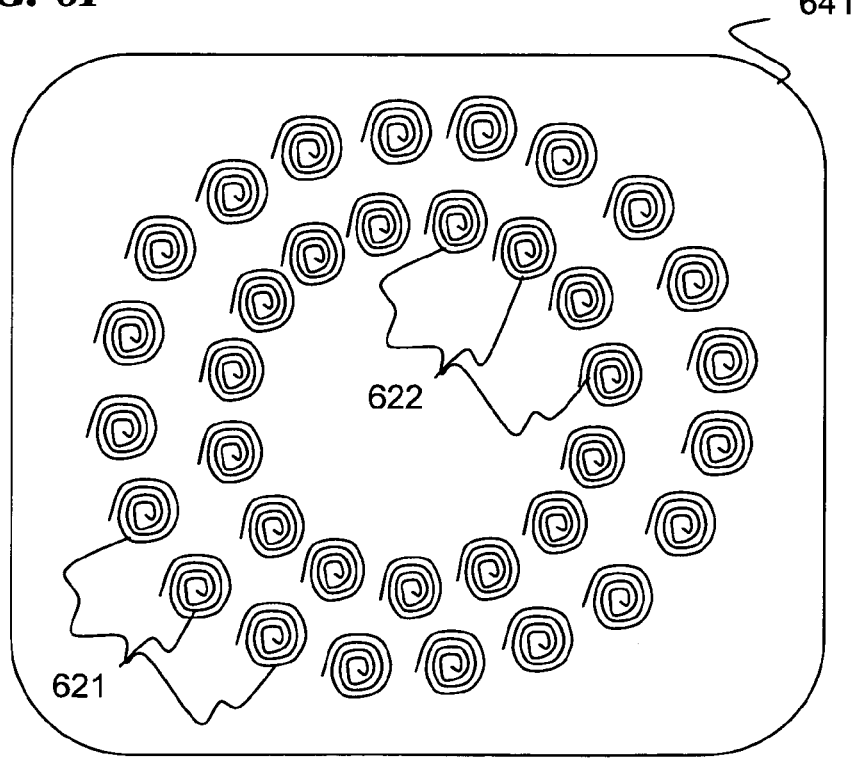
FIG. 6G is a top-view of flex substrate 641 having a plurality of excitation units 621 and 622.

FIG. 6G is a top-view of flex substrate 641 having a plurality of excitation units 621 and 622 arranged in two concentric circular rows. In some embodiments, the outer row of excitation units 621 are used for fasteners having larger circular boundaries, and the inner row of excitation units 622 are used for fasteners having smaller circular boundaries. In other embodiments, one or more different row selections are used for the various-sized fasteners. In yet other embodiments, other numbers of excitation units, other numbers of rows, or other patterns of excitation units (such as a Cartesian arrangement of rows and columns) and the desired subsets of excitation units are selected (e.g., a circular-row pattern of coils selected from a larger set of excitation coils on substrate 641) and used to achieve the desired excitation magnetic field for an arbitrarily-shaped or sized boundary (e.g., driving all selected excitation units of a subset with the same signal phase to drive a uniform alternating magnetic field, or driving different ones of the excitation units with different signal phases to generate traveling-wave, rotating-wave, or other patterns of excitation magnetic fields).

Figure 7A:
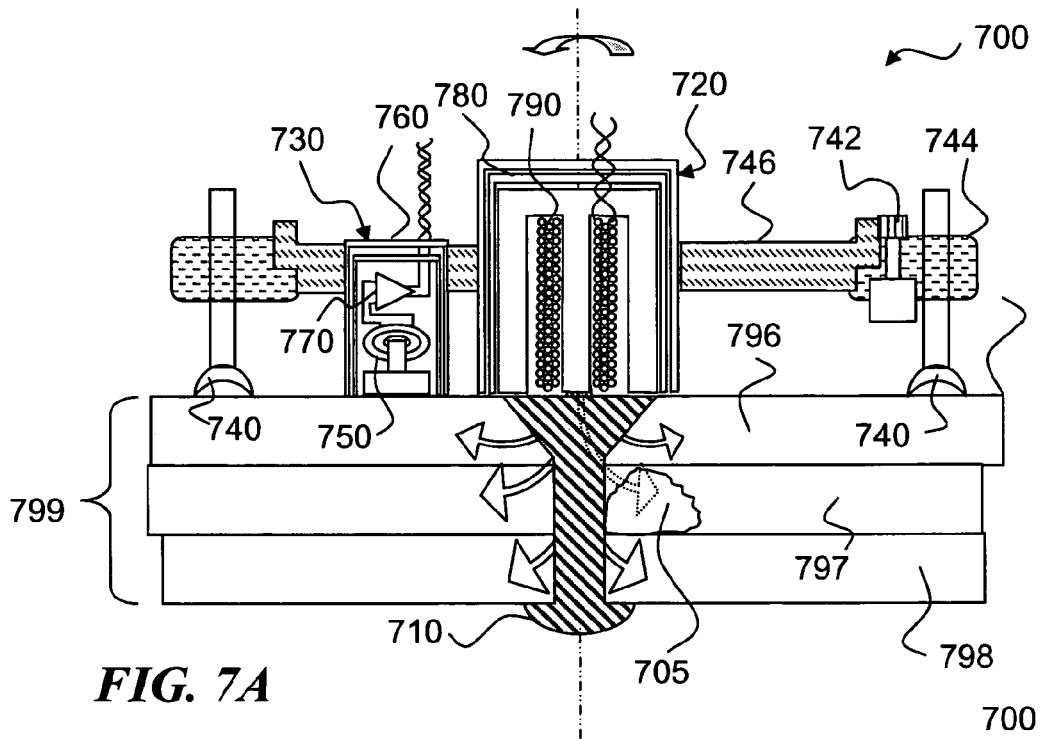
FIG. 7A is a side-view of an apparatus 700 having an attachment structure and a sensor that is configured to be automatically rotated around an excitation unit that is positioned over a structure that penetrates a surface.

FIG. 7A is a cross-sectional elevation side view (along section line 7A shown in FIG. 7B) that illustrates one embodiment of an apparatus or probe 700 of the invention. Probe 700 is positioned on the surface 795 of an object 799 that contains an anomaly 705. The object 799 includes a fastener 710 that penetrates multiple layers 796, 797 and 798 of the object 799. The apparatus 700 includes an excitation unit 720 and a sensor 730. The excitation unit illustrated in FIG. 7A includes one excitation coil 790 and excitation unit shielding 780. The sensor 730 illustrated in FIG. 7A includes an amplifier 770, a coil 750 and sensor shielding 760. The excitation unit 720 and the sensor 730 are operably attached to a rotatable support 746. The rotatable support or platform 746 is operably attached to an immobilization support 744 such that the rotatable support 746 can be rotated by the turning of a drive gear by motor 742. Rotation of the rotatable support 746 causes rotation of the operably attached excitation unit 720 and sensor 730. The immobilization support is operably attached to an immobilization member 740 that can be placed onto a surface 795 of an object 799. A one or more immobilization supports 740 (such as suction cups, permanent magnets, adhesive, tape, screws, and the like) can be used to temporarily attach apparatus 700 of the invention to surface 795 of object 799. Other embodiments omit immobilization supports 740 and are simple set on surface 799 or manually held in place. In FIG. 7A, the excitation unit 720 is shown substantially centered over the fastener 710. An excitation unit 720 and a sensor 730 may also be positioned so that neither is substantially centered over a fastener or other position on the surface of an object 795 as described for FIGS. 3A, 3B and 3C. In FIG. 7A, the sensor 730 is positioned so that it can be rotated around the excitation unit 720 and the fastener 710 to detect the presence of an anomaly 705 that is located below a fastener 710 included within the object 799. Accordingly, use of the apparatus 700 of the invention allows the presence of an anomaly 705 that is hidden below the fastener 710 to be detected.

Figure 7B:
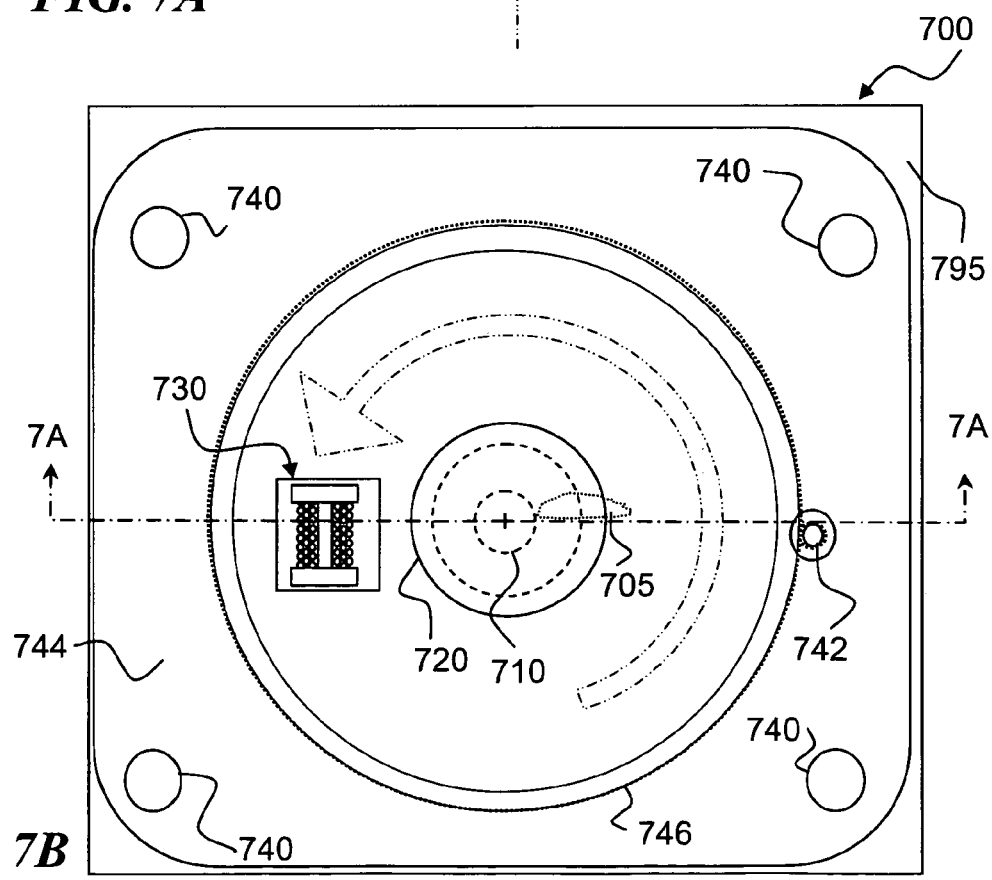
FIG. 7B is a top-view of apparatus 700 having an attachment structure and a sensor that automatically rotates around excitation unit 720 that is positioned over a structure that penetrates a surface.

FIG. 7B is a top view of device 700, which is shown in side cross section in FIG. 7A. More specifically, FIG. 7B illustrates rotation of a rotatable support 746 to which is operably attached a sensor 730 and an excitation unit 720 that emits an AC magnetic field schematically shown as 777. AC field 777 generates eddy currents and magnetic field lines that deviate (shown as dotted arrow) if a crack or other anomaly 705 is encountered. The rotatable support 746 that includes the excitation unit 720 and the sensor 730 is positioned such that the excitation unit is substantially centered on the fastener 710. Rotation of the rotatable support 746 by geared motor 742 rotates platform 746 and causes the sensor 730 to rotate around the excitation unit 720 and the fastener 710 during scanning of the object for the presence of an anomaly 705 contained within the object 799. In other embodiments, motor 742 is omitted and platform 746 is manually rotated, with probe 700 supported at its outer corners by suction-cup immobilization members 740 (or other attachment devices) to surface 795.

Figure 8A:
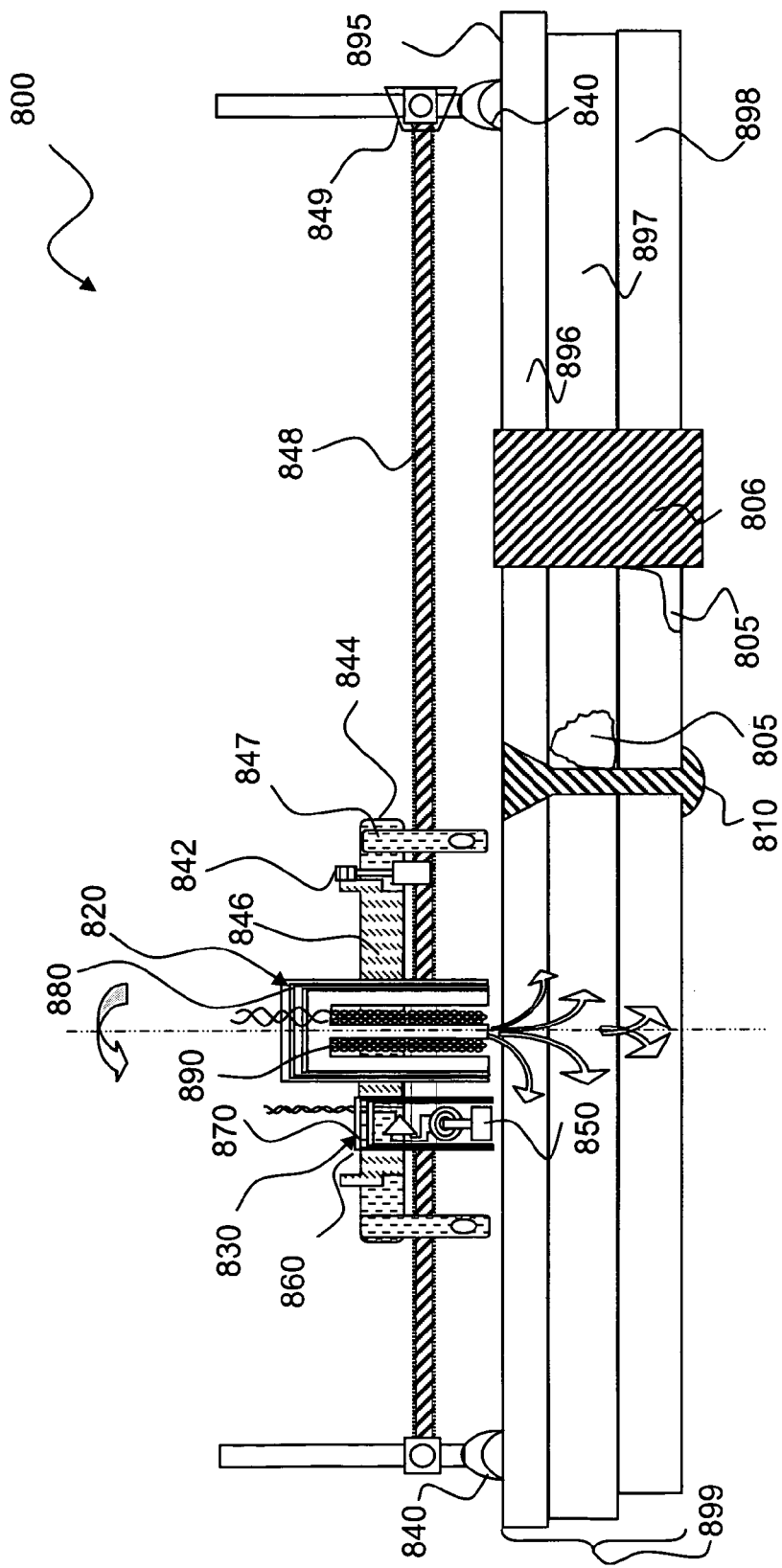
FIG. 8A is a side-view of an apparatus 800 having an attachment means and a sensor that is positioned to be rotated around an excitation unit that is positioned over a structure that penetrates a surface.

FIG. 8A is a cross-sectional elevation side view (along section line 8A shown in FIG. 8B) that illustrates one embodiment of an apparatus or probe 800 of the invention. Probe 800 is positioned on the surface 895 of an object 899 that contains an anomaly 805 and a structure 806. The object 899 includes a fastener 810 that penetrates multiple layers 896, 897 and 898 of the object 899. The apparatus 800 includes an excitation unit 820 and a sensor 830. The excitation unit illustrated in FIG. 8A includes one excitation coil 890 and excitation unit shielding 880. The sensor 830 illustrated in FIG. 8A includes an amplifier 870, a coil 850 and sensor shielding 860. The excitation unit 820 and the sensor 830 are operably attached to a rotatable support 846. The rotatable support 846 is operably attached to a X-Y movable base 844 such that the rotatable support 846 can be rotated by the turning of a drive gear motor 842 (which is rotated under control of a controller such as circumscribe controller 957 shown in FIG. 9). Rotation of the rotatable support 846 causes rotation of the operably attached excitation unit 820 and sensor 830.

The probe's X-Y movable base 844 is operably attached to X-direction sliding guide 841 and X-direction transverse rotatable screw guide 848 (which is rotated by motor 849 under control of a controller such as position controller 956 shown in FIG. 9) through threaded transverse supports 847 that allows X-Y movable base 844 to be placed at any X position on the surface 895 of the object 899. When motor 849 rotates screw 848, base 844 slides along glide 841, and shuttles 852 slide along glides 853. The probe's X-Y movable base 844 is also operably attached to Y-direction sliding guide 851 and Y-direction transverse rotatable screw guide 858 (which is rotated by motor 859 under control of a controller such as position controller 956 shown in FIG. 9) through threaded transverse supports 857 that allows X-Y movable base 844 to be placed at any Y position on the surface 895. When motor 859 rotates screw 858, base 844 slides along glide 851, and shuttles 855 slide along glides 854. This allows the excitation unit 820 and the sensor 830 to be placed at any (X,Y) position on the surface 895 of the object 899 under control of a position controller, and for platform 846 to be rotated to any desired angle (or in a circle) under control of a rotation controlled. The transverse glides 853 and 854 are attached to corner brackets 856 that are operably connected to immobilization members 840 (e.g., suction cups, adhesive, permanent magnets, sticky tape, and the like) that are used to hold apparatus 800 onto surface 895.

Figure 8B:
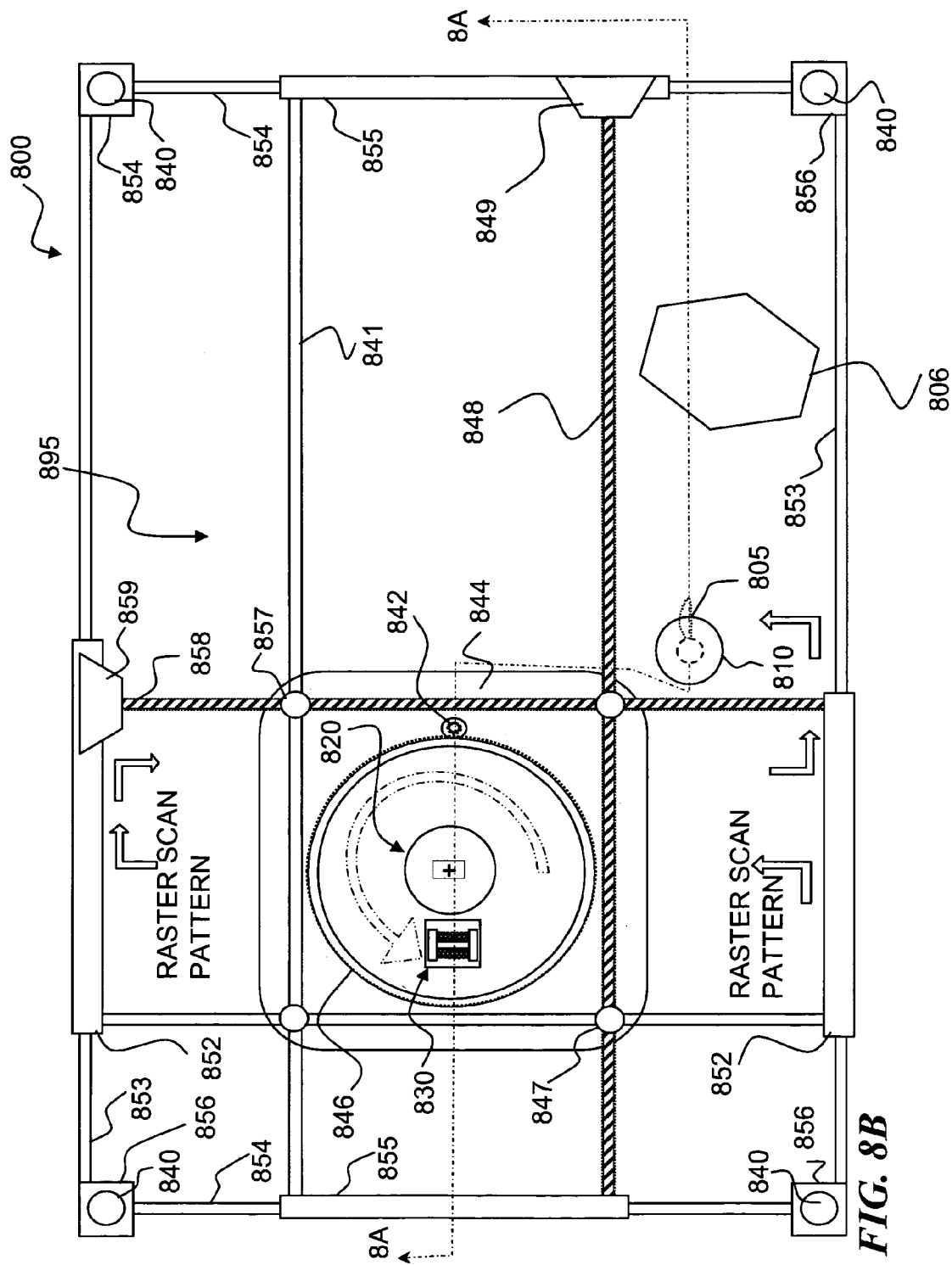
FIG. 8B is a top-view of apparatus 800 having an attachment means and a sensor that rotates around an excitation unit that is positioned over a structure that penetrates a surface.

FIG. 8B is a top view of device 800, which is shown in side cross section in FIG. 8A. As illustrated in FIG. 8B, the transverse glides 853 and 854 are attached to corner brackets 856, and are operably attached to the immobilization members 840. The base 844 can be moved to any (X, Y) position and along any vector by operating motor 849 and 859 simultaneously at appropriate relative speeds, and platform 846 can be rotated to any angle (or series of angles), thus allowing automated scanning of surface 895 to locate and identify borders or outlines of features such as rivet 810 or hexagonal feature 806, for example. When a small circular feature such as rivet 810 is located and identified, base 844 is moved to center the probe over rivet 810 and remain there, and platform 846 is rotated around a circle with excitation unit and sensor 830 in a fixed relationship to the periphery of feature 810 (e.g., with excitation unit 820 centered on rivet 810 and sensor 830 rotated around its edge) to locate flaws 805 that are adjacent to feature 810. When a larger feature such as metal hexagon 806 is located and identified, platform 846 is rotated to an appropriate angle to match a first edge of feature 806, and base 844 is moved along that first edge. Then platform 846 is rotated to an appropriate angle to match each successive edge of feature 806 and base 844 is move along those respective successive edges, thus inspecting the entire periphery of feature 806 to locate flaws 805 that are adjacent to feature 806. When following an edge, the signal should remain substantially constant since the excitation unit and sensor remain in a fixed relationship relative to the edge. As corners are reached, the signal should change in a predicted/predictable manner, so the software of FIG. 9 recognizes these patterns and detects differences between the sensed signal and the expected signal that indicate a flaw next to feature 806. In some embodiments, after following along an edge, when a corner is reached, platform 846 is rotated in an arc around that corner and software analyzes the signal and compares it to an expected signal pattern for such a corner. Accordingly, the base 844 can be positioned at any point along a transverse guides 848 and 858 (i.e., any (X, Y) position), and platform 846 can be positioned at any angle, which allows the excitation unit 820 and the sensor 830 to be moved in complex vector directions combined with angular directions for scanning unknown parts to detect and identify known types of expected features and distinguish flaws located near and/or under those features. A plurality of immobilization members 840 can be used in an apparatus of the invention 800.

In some embodiments, the excitation unit 820 and sensor 830 are positioned so that the excitation unit 820 is substantially centered over a fastener 810 or other position on the surface of an object 895 and the sensor 830 is rotated around the fastener 810 or other position as described for FIGS. 1A, 1B and 1C. Through software control of position and angle, excitation unit 820 and sensor 830 may be positioned and moved so that the sensor 830 remains substantially centered over a fastener or other position on the surface of an object 895 and the excitation unit 820 is rotated around the fastener or other position as described for FIGS. 2A, 2B, and 2C. In other embodiments, probes such as described in FIGS. 2A, 3A, and/or 4A can be substituted for excitation unit 820 and sensor 830 on platform 846 or base 844. An excitation unit 820 and a sensor 830 may also be positioned so that neither is substantially centered over a fastener or other position on the surface of an object 895 as described for FIGS. 3A, 3B and 3C. In FIG. 8A, the sensor 830 is positioned so that it can be rotated around the excitation unit 820 and the fastener 810 to detect the presence of an anomaly 805 that is located below a fastener 810 included within the object 899. Accordingly, use of the apparatus 800 of the invention allows the presence of an anomaly 805 that is hidden below the fastener 810 to be detected. The apparatus 800 illustrated in FIG. 8A and FIG. 8B can be used to scan an object 899 for an anomaly 805 that may be present in the object 899. Furthermore, the apparatus 800 allows a structure 806 present in an object 899 to be scanned. This can be accomplished by positioning the immobilization support 844 at multiple positions around the structure 806 such that the excitation unit 820 and the sensor 830 that are operably attached to the immobilization support 844 can be used to detect an anomaly that may be present in the object 899 adjacent to the structure 806.

FIG. 9 is a schematic diagram of an apparatus 900 according to one embodiment of the present invention. Apparatus 900 includes an eddy-scope 901 (i.e., a computer and/or electronics that provide excitation signal 936 and optionally motor control signals to provide X position, Y position, and angle motion control, and which receives signal 937 and analyzes magnitude and phase and compares these against expected values, for example, stored in a table from empirical measurements of known good parts and parts having known flaws or other anomalies, or derived from an empirically or analytically derived formula) and probe 951 coupled by a shielded electrical connector. Eddy-scope 901 includes excitation driver 931, power supply 932, phase/amplitude detection and presentation circuit 934, display 954, controls 955, position controller 956, optional circumscribe controller 957, and an optional audio alert 935. Excitation driver circuit 931 provides one or more phases of excitation signal 936 to drive one or more excitation coils 920 in probe 951. Power supply 932 provides electrical power 938 to drive amplifier 920 within probe 951, as well as to other components of eddy-scope 901. Phase and amplitude detection and presentation circuit 934 receives phase signal 933, and conditioned sensor signal 937, and, in one embodiment, generates a signal to display 954 that includes real and/or imaginary components of the sensor signal 937. In some embodiments, distance or time is plotted horizontally on the output display, and real and/or imaginary amplitude is plotted vertically. In some embodiments, the amplitude is plotted on one axis (e.g., horizontally), and the phase is plotted on the other axis (e.g., vertically). In other embodiments, the amplitude of the real component is plotted on one axis (e.g., horizontally), and the amplitude of the imaginary component is plotted on the other axis (e.g., vertically). Sensor 951 further includes shielding 960 and 980, which in various embodiments includes one or more layers of shielding made of such materials as aluminum, copper, steel, and/or other suitable magnetic and electrically shielding materials. In some embodiments, sensor or sensors 930 include sensor coils mounted on a ferromagnetic core. Excitation coil or coils 920 typically include a ferromagnetic core and one or more coils of wire.

In various embodiments, display 954 includes one or more graphical displays of phase and amplitude or the relative phases of the output and input signals, and/or other indications of the real and imaginary portions of the received signal 937, as compared to a phase reference 933 of the excitation driver. These displayed signals are used to detect anomalies in the scanned object being tested. Various embodiments of the present invention are used to scan the metal surfaces of materials such as airplane wings having rivets and/or paint 958 and applique 959 surfaces under which the metal is being tested for cracks or other indications of failure or fatigue.

Figure 10A:
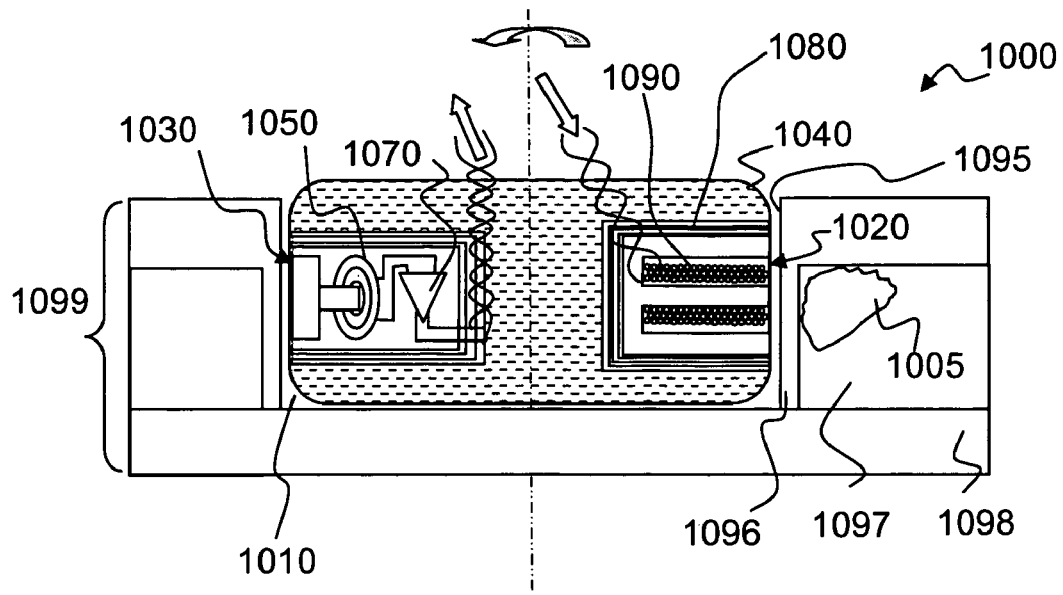
FIG. 10A is a side-view of an apparatus 1000 having a sensor and an excitation unit 1020 positioned in a probe protrusion that fits in a structure 1010 having an opening that penetrates a surface of an object, the probe configured to be rotated around inside structure 1010.
Figure 10B:
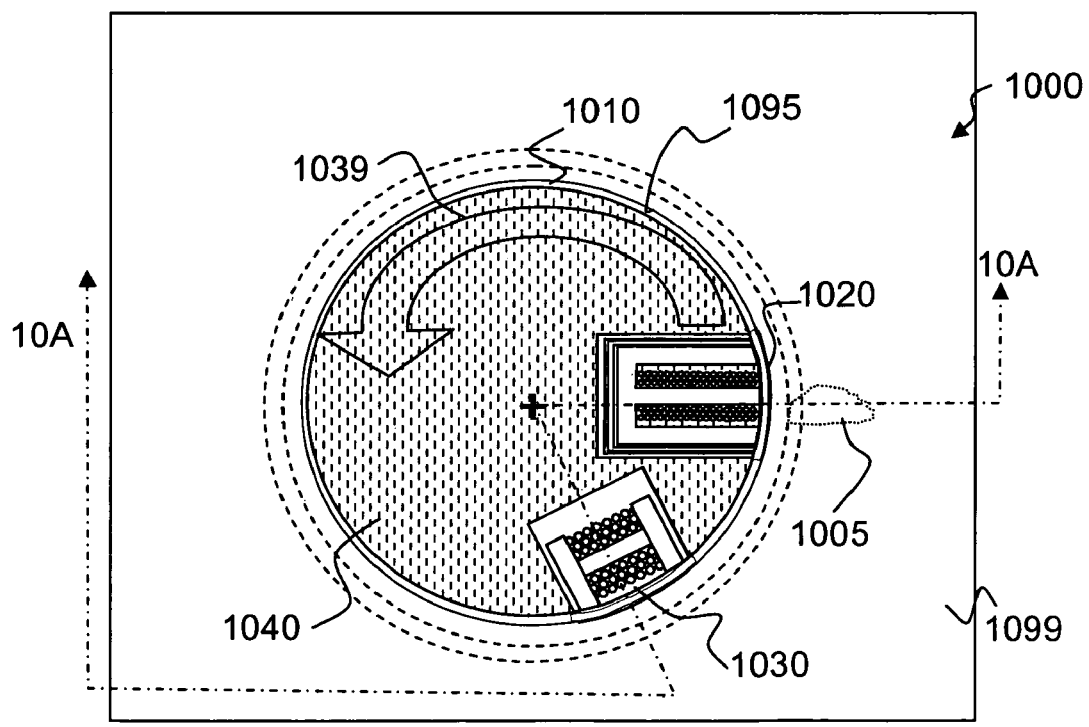
FIG. 10B is a top-view of apparatus 1000 having a sensor and excitation unit that rotate around an inner surface of a structure 1010 that penetrates a surface of an object.

FIG. 10A is a side-view of an apparatus 1000 having a sensor 1030 and an excitation unit 1020 positioned in a probe protrusion or housing 1040 that fits in indented or hollow structure 1010 having an opening that penetrates a surface of an object, the probe 1000 configured to be rotated around inside structure 1010. Structure 1010 can have an opening that has cylindrical walls and a floor, or can be a through-hole structure. In some embodiments, probe protrusion or housing 1040 is sized to nearly fill the entire opening in structure 1010, while in other embodiments, probe protrusion or housing 1040 is smaller (e.g., an arc or slice-of-pie shape having a curved outer section that matches the curve of the opening in structure 1010) and only fills a portion of the opening. In some embodiments, one or more EU coils and one or more sensor coils are fabricated on a piece of flex circuit substrate (e.g., such as shown in FIG. 6E) that is configured to conform to an inside surface of the opening in structure 1010. Object 1099 is fabricated using a plurality of layers or pieces 1098, 1097, 1096, and flaw or anomaly 1005 is on a surface or within one or more of these layers or pieces. In some embodiments, more than one sensor 1030 and/or more than one excitation unit 1020 are included (positioned either at each of a plurality of different depths, at each of a plurality of different angular locations, at both plural depths and plural angles and/or across the bottom surface of probe 1000 (e.g., to scan the floor of the opening)), and are electrically driven or scanned to effect moving the EU signal sent or the sensor signal received without physically moving probe 1000 or to sense each of a plurality of locations simultaneously FIG. 10B is a top-view of apparatus 1000 having a sensor and excitation unit that rotate around (e.g., following path 1039 an inner surface of a structure 1010 that penetrates a surface of an object in order to locate flaw 1005 under surface 1095 of the inner portion of hole 1010. In the embodiment shown, excitation unit 1020 is at one angular position, while sensor 1030 is at a different angular position to the, side of EU 1020. In other embodiments, one or more EUs 1020 and/or one or more sensors 1030 are located at a plurality of different depths and/or angles.

In some embodiments of any of the above descriptions, the plurality of sensors (Ss) and excitation units (EUs) are implemented as printed-circuit coils fabricated on a thin flexible substrate. In some embodiments, the same coil can be used both as excitation unit coils and sensor coil. In some embodiments, a plurality of such flexible printed circuits are layered one upon another. In some embodiments, in order to detect anomalous signal changes (signal changes due to a crack or other anomaly) around the structure in a manner that reduces signal changes due to a boundary between the structure and the surface, one or more individual ones of a subset of the excitation units are driven in order to generate an excitation field, and one or more individual ones of a subset of the sensors are sensed under control of the controller. In some embodiments, excitation units are local and/or global and driven to generate a field that covers the whole area under inspection. In some embodiments, one or more individual ones of a subset of the excitation units are driven to generate a traveling/rotational magnetic field. In some embodiments, one or more individual ones of a subset of the excitation units and/or one or more individual ones of a subset of the sensors are formed as separate arrays that are not necessarily built on a single layer.

In some embodiments, the invention includes one or more excitation units, and one or more sensors, wherein the apparatus is configured (by physical movement or by electronic manipulation of the signal to the EUs and/or by electronic processing of the signals from the sensor(s)) to "scan" a surface of the object (e.g., an aircraft wing or helicopter rotor or boom) having a structure (e.g., a rivet), in order to detect anomalous signal changes (signal changes due to a crack or other anomaly) around the structure in a manner that reduces signal changes due to a boundary between the structure and the surface. For example: (1) some embodiments rotate sensor while keeping EU centered on rivet (FIG. 1B shows this generally), some embodiments of FIG. 5A have a dimple in the EU that fits over a raised-head rivet to keep the EU from moving sideways as it rotates the sensor, some embodiments of FIG. 5D have a sharp point 529 on the EU core that provides a pivot point to press against the flat-head rivet 511, and around which to rotate the sensor, and some embodiments of FIG. 7B use suction cups 740 or magnets or adhesive (e.g., sticky tape) on a base 744 that is manually placed to center EU on rivet to hold the outside base 744 unmovable on the surface while a circular center platform 746 moves in a circle (either manually rotated or rotated by gear and motor 742)-this eliminates need to touch rivet as in FIG. 5A or FIG. 5D, which could scratch aircraft skin (some embodiments of FIG. 8B can also do this once platform 844 is moved to center of rivet by X,Y motors); example (2) some embodiments rotate EU while keeping sensor centered on the rivet (FIG. 2B shows this, FIG. 7B can do this by swapping positions of sensor and EU, FIG. 8B could do this by either swapping positions of sensor and EU, or by a combination of X,Y and rotation motor movements); example (3) some embodiments rotate EU and sensor around a non-moving point centered on rivet, and to side of both EU and sensor centered on rivet (FIG. 3B shows this, FIG. 7B could do this by moving positions of sensor and EU to the side, FIG. 8B could do this by either moving positions of sensor and EU, or by a combination of X,Y and rotation motor movements); example (4) some embodiments move EU fields electronically using non-moving EUs and sensor(s) (FIG. 6B and FIG. 6E show this) example (5) some embodiments switch which positions are sensed electronically using non moving EU(s) and sensors (FIG. 4B shows this); example (6) some embodiments move EU fields electronically using non-moving EUs and sensor(s) and switch which positions are sensed electronically using non-moving EU(s) and sensors (FIG. 6D and FIG. 6E show this, FIG. 6E is just a generalized block diagram of an array of EUs and sensors—in other embodiments, they are in Cartesian rows and columns, or superimposed on one another, and in other embodiments, EU and sensor functions are accomplished both in a single coil); example (7) some embodiments use mechanical X,Y scanning and/or rotation of platform 846 (or electronic means such as example 6) to locate rivet(s), then use any one of the above techniques to scan the border of the rivet while preventing border-crossing effects, in order to detect flaws next to rivet. In some embodiments, the invention provides new and unique specific ways of using one or more EUs and one or more sensors to locate a rivet and then scan in a circle around the rivet to avoid boundary crossing. These are non-limiting descriptions of some examples of the invention. It is the language of claims as a whole that define the invention. The physical block-diagram examples of FIGS. 1-10 are just generalized examples of how to accomplish this.

Some embodiments of he invention provides an apparatus that includes a magnetically shielded excitation unit that generates an alternating excitation magnetic signal; and one or more magnetically shielded sensors that are positioned adjacent the excitation unit and that are configured to detect a remote-field eddy-current signal due to the excitation magnetic signal, wherein the apparatus is configured to scan a surface having a structure in order to detect anomalous signal changes around the structure in a manner that reduces signal changes due to a boundary between the structure and the surface.

In some embodiments, the apparatus is configured to scan the surface with the excitation unit substantially centered over the structure. In some embodiments, the apparatus is configured to scan the surface with the excitation unit substantially centered over the structure by physically moving the one or more sensors around the structure. In some embodiments, the apparatus is configured to scan the surface with the excitation unit substantially centered over the structure by physically moving the one or more sensors in a circle around the structure.

Some embodiments of the apparatus include a plurality of the magnetically shielded sensors that are positioned around the structure and the apparatus is configured to scan the surface around the structure by analyzing signals from the plurality of the magnetically shielded sensors without physically moving the one or more sensors around the structure. Some embodiments of the apparatus include a plurality of magnetically shielded sensors that are positioned substantially along a circle around the structure and the apparatus is configured to scan the surface around the structure by analyzing signals from the plurality of the magnetically shielded sensors without physically moving the one or more sensors around the structure. In some embodiments of the apparatus, one or more sensors are configured to be rotated around a point substantially centered on the one or more excitation units. In some embodiments of the apparatus, the apparatus includes a plurality of sensors that are positioned around the one or more excitation units.

In some embodiments of the apparatus, the apparatus is configured to scan the surface with one of the one or more sensors substantially centered over the structure. In some embodiments, the apparatus is configured to physically move the excitation unit around the one or more sensors in order to scan the surface next to the structure. In some embodiments, the apparatus is configured to physically move the excitation unit in a circle around the one or more sensors in order to scan the surface next to the structure.

In some embodiments, the apparatus is configured to move the alternating excitation magnetic signal generated by the excitation unit as a traveling wave along a path around the structure in order to scan the surface next to the structure. In some embodiments, the apparatus is configured to move the alternating excitation magnetic signal generated by the excitation unit as a traveling wave along a circle around the structure in order to scan the surface next to the structure. In some embodiments of the apparatus, the excitation unit includes a plurality of electromagnetic coils each driven by a different phase of an alternating electric signal to form the alternating excitation magnetic signal generated by the excitation unit as a traveling wave along a path around the structure in order to scan the surface next to the structure. In some embodiments, the excitation unit includes a plurality of electromagnetic coils each driven by a different phase of an alternating electric signal to form the alternating excitation magnetic signal generated by the excitation unit as a traveling wave along a circle around the structure in order to scan the surface next to the structure. In some embodiments, the one or more excitation units are configured to be rotated around a point substantially centered on one of the one or more sensors. In some embodiments, the one or more excitation units are configured to be rotated around a point to a side of the one or more excitation units and to a side of the one or more sensors. In some embodiments, the excitation unit is one of a plurality of excitation units that are positioned around the one or more sensors.

In some embodiments of the apparatus, neither the one or more sensors nor the excitation unit are configured to be positioned over the structure. In some embodiments, the one or more sensors and the excitation unit are configured to be moved around a point centered on the structure. In some embodiments, the one or more sensors and the excitation unit are configured to be moved along respective circles around a point substantially centered on the structure. In some embodiments, the apparatus is configured for the one or more sensors to be rotated around the structure. In some embodiments, the apparatus is configured for the one or more sensors to be rotated in a circle around the structure. In some embodiments, the apparatus is configured for the excitation unit to be rotated around the structure. In some embodiments, the apparatus is configured for the excitation unit to be rotated in a circle around the structure.

In some embodiments, the structure does not penetrate the surface. In some embodiments, the structure penetrates the surface. In some embodiments, the surface is a face of one layer of a stack of layers. In some embodiments, the structure is a fastener. In some embodiments, the fastener is a screw. In some embodiments, the fastener is a bolt. In some embodiments, the fastener is a rivet. In some embodiments, the fastener is a grommet. In some embodiments, the fastener is a pin.

In some embodiments, the surface is metallic. In some embodiments, the surface includes a metal. In some embodiments, the surface is a composite. In some embodiments, the structure is metallic. In some embodiments, the structure includes a metal. In some embodiments, the structure is a composite.

In some embodiments of the apparatus, at least one of the one or more sensors is a differential sensor. In some embodiments, the apparatus further includes a display. In some embodiments, the display indicates when the excitation unit is substantially centered over the structure. In some embodiments, the display indicates the position of an anomaly in the surface.

In some embodiments of the apparatus, the one or more sensors includes a plurality of sensors that are positioned around the excitation unit and the apparatus is configured to use the plurality of sensors to find a location of a subsurface anomaly in a surface without rotating the apparatus.

In some embodiments, the apparatus includes an attachment mechanism to attach the apparatus at a location on the surface. In some embodiments, the apparatus includes a moving mechanism to move at least a portion of the apparatus to a position over the structure. In some embodiments, the apparatus includes an information processor configured to automatically analyze signals from the one or more sensors and to control the moving mechanism to move the portion of the apparatus to the position over the structure.

The invention provides a method that includes forcing an alternating excitation magnetic field into a surface, detecting a remote-field eddy-current signal resulting from the alternating excitation magnetic field at each of a plurality of positions on the surface surrounding a structure on the surface in a manner that reduces signal changes due to a boundary between the structure and the surface; and analyzing the detected signal from the plurality of positions to determine whether the surface contains an anomaly next to the structure. In some embodiments, the structure penetrates the surface.

In some embodiments, the method further includes maintaining the alternating excitation magnetic field so it remains substantially centered on the structure. In some embodiments, the detecting of the remote-field eddy-current signal resulting from the alternating excitation magnetic field at each of the plurality of positions surrounding the structure includes positioning a plurality of sensors that each are substantially centered on each respective one of the plurality of positions on the surface. In some embodiments, the detecting of the remote-field eddy-current signal at each of the plurality of positions surrounding the structure, and the forcing of the alternating excitation magnetic field into the surface, are performed at a position that is not substantially centered on the structure. In some embodiments, the forcing of the alternating excitation magnetic field into the surface is performed substantially centered on the structure.

In some embodiments, the method includes detecting the remote-field eddy-current at a position that is substantially centered on the structure. In some embodiments, the method includes detecting the remote-field eddy-current and forcing an alternating excitation magnetic field into a surface at a position that is not substantially centered on the structure. In some embodiments, the method includes forcing an alternating excitation magnetic field into a surface at a position that is around each one of the plurality of positions on the surface. In some embodiments, the method includes forcing an alternating excitation magnetic field into a surface at a position that is around the structure.

In some embodiments, the method includes generating a rotating magnetic field around a position on the surface. In some embodiments, the method includes examining phase and amplitude values of the remote-field eddy current to determine if the surface includes an anomaly. In some embodiments, the method includes identifying the anomaly as a crack. In some embodiments, the method includes identifying the anomaly as a fissure. In some embodiments, the method includes identifying the anomaly as a scratch. In some embodiments, the method includes identifying the anomaly as erosion. In some embodiments, the method includes identifying the anomaly as thinning. In some embodiments, the method includes identifying the anomaly as a hole. In some embodiments, the method includes identifying the anomaly as an opening. In some embodiments, the method includes identifying the anomaly as a cavity. In some embodiments, the method includes identifying the anomaly as a different metal.

The invention provides a method that includes providing an apparatus that includes an excitation unit and one or more sensors next to the excitation unit; shielding the excitation unit and the one or more sensors to minimize detection of signals other than remote-field eddy-current signals by the one or more sensors; and configuring the excitation unit and the one or more sensors to detect anomalous signal changes around a structure in a surface in a manner that reduces signal changes due to a boundary between the structure and the surface.

In some embodiments of the method, the one or more sensors include at least one differential sensor. In some embodiments, the method includes configuring the apparatus so that the one or more sensors are rotated around the excitation unit. In some embodiments, the method includes configuring the apparatus so that the excitation unit is rotated around the one or more sensors. In some embodiments, the method includes configuring the excitation unit and the one or more sensors to be independently rotatable. In some embodiments, the method includes configuring the one or more excitation units and the one or more sensors in a fixed position relative to one another.

In some embodiments, the method includes coupling the one or more sensors to an analysis unit that analyzes a signal from the one or more sensors. In some embodiments of the method, neither the excitation unit nor the one or more sensors are moved relative to the structure.

In some embodiments, the method includes configuring the apparatus to automatically scan the surface to locate the structure. In some embodiments, the method includes configuring the apparatus to automatically scan the surface around the structure.

The invention provides an apparatus that includes means for forcing an alternating excitation magnetic field into a surface; means for detecting a remote-field eddy-current signal resulting from the alternating excitation magnetic field at each of a plurality of positions on the surface surrounding a structure in the surface in a manner that reduces signal changes due to a boundary between the structure and the surface; and means for analyzing the detected signal from the plurality of positions to determine whether the surface contains an anomaly next to the structure.

In some embodiments, the means for detecting the remote-field eddy-current signal resulting from the alternating excitation magnetic field at each of the plurality of positions surrounding the structure includes a plurality of sensors that are each located at a respective one of the plurality of positions around the excitation unit. In some embodiments, neither the means for detecting the remote-field eddy-current signal at each of the plurality of positions surrounding the structure, nor the means for forcing the alternating excitation magnetic field into the surface, are substantially centered on the structure. In some embodiments, the means for forcing the alternating excitation magnetic field into the surface is substantially centered on the structure.

In other embodiments, the apparatus includes means to attach the apparatus at a location on the surface. In some embodiments, the apparatus includes means to move at least a portion of the apparatus to a position over the structure. In some embodiments, the apparatus includes means for analyzing signals from the one or more sensors and to control the moving mechanism to move at least a portion of the apparatus to a position over the structure.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," "third," and the like are used merely as labels, and are not intended to impose numerical requirements on their objects

What is claimed is:

1. An apparatus comprising:
   an excitation unit that generates an alternating magnetic excitation signal; and
   one or more magnetic sensors that are positioned adjacent the excitation unit and that are configured to detect a signal due to the excitation magnetic signal interacting with an object being inspected, wherein the apparatus is configured to scan a surface of the object having a structure in order to detect anomalous signal changes around the structure in a manner that reduces signal changes due to a boundary between the structure and the surface;
   a position actuator;
   a rotation actuator;
   a controller operatively coupled to the position actuator and the rotation actuator, and operable to move and angle the excitation unit and the one or more sensors in order to detect a position of the structure and to control the excitation unit and the one or more sensors to detect an anomaly next to the structure;
   an information processor configured to receive and to automatically analyze signals from the one or more sensors and to control the controller to move the portion of the apparatus to the position over the structure.

2. The apparatus of claim 1, wherein the apparatus is configured to scan the surface with the excitation unit substantially centered over the structure.

3. The apparatus of claim 1, wherein the apparatus is configured to move the alternating excitation magnetic signal generated by the excitation unit as a traveling wave along a path around the structure in order to scan the surface next to the structure.

4. The apparatus of claim 1, further comprising a display, wherein the display indicates when the excitation unit is substantially centered over the structure.

5. The apparatus of claim 1, further comprising a display, wherein the display indicates a position of the anomaly.

6. The apparatus of claim 1, further comprising an attachment mechanism to attach the apparatus at a location on the surface.

7. The apparatus of claim 1, wherein the structure is a fastener having a center, and wherein the rotation actuator is configured to rotate the excitation unit and the one or more sensors along a circular path centered on the center of the fastener.

8. A method comprising:
providing an apparatus comprising an excitation unit and one or more sensors next to the excitation unit;
shielding the excitation unit and the one or more sensors to minimize detection of signals other than remote-field eddy-current signals by the one or more sensors;
configuring the excitation unit and the one or more sensors to detect anomalous signal changes around a structure in a surface in a manner that reduces signal changes due to a boundary between the structure and the surface;
positioning and rotating the excitation unit and one or more sensors to locate the structure using one or more controlled actuators;
configuring the apparatus so that the one or more sensors are rotated around the excitation unit; and
displaying a result that indicates a position of an anomaly next to the structure.

9. The method of claim 8, wherein the one or more sensors includes at least one differential sensor.

10. The method of claim 8, wherein the one or more sensors include a first sensor and wherein the first structure is a fastener having a center, the method further comprising:
rotating the first sensor and the excitation unit along a circular path centered on the center of the fastener using the one or more controlled actuators; and
displaying a result that indicates whether there is an anomaly next to the structure.

11. The method of claim 8, wherein the one or more sensors include a first sensor and wherein the first structure is a fastener having a center, the method further comprising:
centering a center of the excitation unit on a center of the fastener using the one or more controlled actuators;
rotating the first sensor along a circular path centered on the center of the fastener using the one or more controlled actuators; and
displaying a result that indicates whether there is an anomaly next to the structure.

12. The method of claim 8, wherein the one or more sensors include a first sensor and wherein the first structure is a fastener having a center, the method further comprising:
centering a center of the first sensor on a center of the fastener using the one or more controlled actuators;
rotating the excitation unit along a circular path centered on the center of the fastener using the one or more controlled actuators; and
displaying a result that indicates whether there is an anomaly next to the structure.

13. An apparatus comprising:
an excitation unit that generates an alternating magnetic excitation signal; and
one or more magnetically shielded magnetic sensors that are positioned adjacent the excitation unit and that are configured to detect a signal due to the excitation magnetic signal interacting with an object being inspected, wherein the apparatus is configured to scan a surface of the object having a structure in order to detect anomalous signal changes around the structure in a manner that reduces signal changes due to a boundary between the structure and the surface, wherein the apparatus is configured to scan the surface with the excitation unit substantially centered over the structure, and wherein the apparatus is configured with a recess on the excitation unit, wherein the recess conforms to a protrusion of the structure configured to assist keeping the excitation unit substantially centered over the structure during a rotation of the apparatus.

14. The apparatus of claim 13, wherein the apparatus is configured to scan the surface with the excitation unit substantially centered over the structure by physically moving the one or more sensors around the structure.

15. The apparatus of claim 13, wherein the apparatus is configured to scan the surface using at least a first scan pattern to locate the structure, and using a second scan pattern that maintains the excitation unit substantially centered over the structure and physically moving the one or more sensors in a circle around the structure.

16. The apparatus of claim 13, wherein the one or more magnetically shielded magnetic sensors include a plurality of the magnetically shielded magnetic sensors that are positioned around the structure and the apparatus is configured to scan the surface around the structure by analyzing signals from the plurality of the magnetically shielded sensors without physically moving the one or more sensors around the structure.

17. The apparatus of claim 13, further comprising a motor, and wherein the one or more sensors are configured to be rotated around a point substantially centered on a center axis of the excitation unit using the motor.

18. The apparatus of claim 13, wherein the apparatus is configured to physically move the excitation unit around the one or more sensors in order to scan the surface next to the structure.

19. The apparatus of claim 13, wherein the excitation unit is configured to be rotated around a point that is radially offset by a first distance from a center axis of the excitation unit and that is radially offset by a distance equal to the first distance from a center axis of the one or more sensors.

20. An apparatus comprising:
an excitation unit that generates an alternating magnetic excitation signal; and
one or more magnetically shielded magnetic sensors that are positioned adjacent the excitation unit and that are configured to detect a signal due to the excitation magnetic signal interacting with an object being inspected, wherein the apparatus is configured to scan a surface of the object having a structure in order to detect anomalous signal changes around the structure in a manner that reduces signal changes due to a boundary between the structure and the surface, wherein the apparatus is configured to scan the surface with the excitation unit substantially centered over the structure, and wherein the apparatus is configured with a protruding point on the excitation unit, wherein the protruding point is configured to assist keeping the excitation unit substantially centered over the structure during a rotation of the apparatus.

21. A method comprising:
forcing an alternating excitation magnetic field into a surface;
detecting a signal resulting from the alternating excitation magnetic field at each of a plurality of relative positions surrounding a structure in a manner that reduces signal changes due to a boundary between the structure and the surface;
analyzing the detected signal from the plurality of positions to determine whether the surface contains an anomaly next to the structure;
maintaining a location of the forcing of the alternating excitation magnetic field such that the excitation magnetic field remains substantially centered on the structure;

providing an excitation unit to perform the forcing of the alternating excitation magnetic field into the surface, wherein the excitation unit has a recess;

providing a sensing unit to perform the detecting of the signal resulting from the alternating excitation magnetic field, and wherein the maintaining of the location of the forcing of the alternating excitation magnetic field includes maintaining the recess of the excitation unit in position on a protrusion of the surface while rotating the sensing unit around the excitation unit.

22. The method of claim 21, wherein the structure is a fastener having a center, wherein the forcing of the alternating excitation magnetic field into the surface is performed at a plurality of respective positions surrounding the fastener that are each offset from a respective one of the plurality of relative positions surrounding the structure at which the detecting of the signal resulting is performed.

23. The method of claim 21, wherein the forcing of the magnetic field includes generating a rotating magnetic field around a position on the surface, and wherein the detecting of the signal resulting from the alternating excitation magnetic field includes detecting a remote-field eddy-current at a position that is substantially centered on the structure.

24. The method of claim 21, further comprising examining phase and amplitude values of a remote-field eddy current signal to determine if the surface includes an anomaly.

25. The method of claim 21, further comprising scanning the surface using at least a first scan pattern to locate the structure, and wherein the maintaining of the location of the forcing of the alternating excitation magnetic field includes scanning the surface using at least a second scan pattern.

26. The method of claim 21, wherein the providing of the sensing unit includes maintaining the recess of the excitation unit in position on the protrusion without physically moving the sensing unit around the structure.

27. The method of claim 21, wherein the providing of the sensing unit includes configuring the sensing unit to be rotated around a point substantially centered on a center axis of the excitation unit.

28. A method comprising:

forcing an alternating excitation magnetic field into a surface;

detecting a signal resulting from the alternating excitation magnetic field at each of a plurality of relative positions surrounding a structure in a manner that reduces signal changes due to a boundary between the structure and the surface;

analyzing the detected signal from the plurality of positions to determine whether the surface contains an anomaly next to the structure;

maintaining a location of the forcing of the alternating excitation magnetic field such that the excitation magnetic field remains substantially centered on the structure;

providing an excitation unit to perform the forcing of the alternating excitation magnetic field into the surface, wherein the excitation unit has a protruding point;

providing a sensing unit to perform the detecting of the signal resulting from the alternating excitation magnetic field, and wherein the maintaining of the location of the forcing of the alternating excitation magnetic field includes maintaining the protruding point on the excitation unit in position on the surface while rotating the sensing unit around the excitation unit.

29. The method of claim 28, further comprising examining phase and amplitude values of a remote-field eddy current signal to determine if the surface includes an anomaly.

\* \* \* \* \*